United States Patent [19]

Kossak et al.

[11] Patent Number: 5,678,578
[45] Date of Patent: Oct. 21, 1997

[54] FLOSSING EQUIPMENT AND METHOD OF OPERATION

[75] Inventors: Michael Kossak, 1634 I Street, NW., Washington, D.C. 20006; Richard Daley, Scituate, R.I.; Ted Lubin, Boston, Mass.; Douglas Schultheis, Cumberland; Paul Kotowski, Foster, both of R.I.; Bernard A. Fitzmorris, Washington, D.C.

[73] Assignee: Michael Kossak, Chevy Chase, Md.

[21] Appl. No.: 635,854

[22] Filed: Apr. 22, 1996

Related U.S. Application Data

[63] Continuation of Ser. No. 267,939, Jul. 6, 1994, abandoned, which is a continuation-in-part of Ser. No. 101,071, Aug. 3, 1993, abandoned.

[51] Int. Cl.⁶ ................................................. A61C 15/00
[52] U.S. Cl. ...................................... 132/322; 132/325
[58] Field of Search ................................ 132/322, 324, 132/325, 326, 327

[56] References Cited

U.S. PATENT DOCUMENTS

| | | |
|---|---|---|
| D. 251,859 | 5/1979 | Kent . |
| 1,700,550 | 1/1929 | Stafford ............................. 132/325 |
| 3,106,216 | 10/1963 | Kirby . |
| 3,340,881 | 9/1967 | Cowan . |
| 3,472,247 | 10/1969 | Borsum et al. . |
| 3,534,745 | 10/1970 | Waters . |
| 3,667,483 | 6/1972 | McCabe . |
| 3,734,107 | 5/1973 | Thierman . |
| 3,746,017 | 7/1973 | Casselman . |
| 3,759,274 | 9/1973 | Warner . |
| 3,908,677 | 9/1975 | Beach . |
| 3,927,687 | 12/1975 | Thierman ............................. 132/325 |
| 4,031,908 | 6/1977 | Ting . |
| 4,235,253 | 11/1980 | Moore . |
| 4,245,658 | 1/1981 | Lecourturier . |
| 4,319,595 | 3/1982 | Ulrich . |
| 4,326,549 | 4/1982 | Hinding . |
| 4,458,702 | 7/1984 | Grollimund . |
| 4,518,000 | 5/1985 | Leverette . |

(List continued on next page.)

FOREIGN PATENT DOCUMENTS

| | | |
|---|---|---|
| 1000533 | 11/1976 | Canada ............................. 132/325 |
| WO 90/11057 | 10/1990 | European Pat. Off. . |
| 0 453 418 | 10/1991 | European Pat. Off. . |
| 3625991 | 2/1988 | Germany . |
| 139048 | 4/1980 | Taiwan . |
| 52610 | 12/1982 | Taiwan . |
| 098442 | 5/1986 | Taiwan . |
| 2141935 | 1/1985 | United Kingdom . |

*Primary Examiner*—Cary E. O'Connor
*Attorney, Agent, or Firm*—Lowe, Price, LeBlanc & Becker

[57] ABSTRACT

A dental flossing device is characterized by a flossing circuit comprising a floss supply spool and a take-up spool mounted to a housing containing a gear train assembly adapted to rotate the take-up spool in a winding direction. The floss feeds from the supply spool along a pair of prongs forming a forked extension of the handle and is stretched across the forked prongs and appropriately tensioned to be inserted into a user's mouth for flossing. To maintain hygiene, the take-up spool is mounted outside the housing. In a manually operated embodiment, a manually depressible trigger projecting from the housing is operable to rotate the take-up spool with reverse rotation thereof being prevented with a ratchet mechanism. Release of the manually depressible trigger reversely rotates the supply spool through a short arcuate interval to remove slack and then locks the supply spool against unwinding rotation through gear teeth. In a preferred manually operated embodiment, first and second ratchet mechanisms are utilized to prevent reverse rotation of the supply and take-up spools while sufficiently tensioning the floss circuit. In other embodiments, the housing may be formed for mounting the flossing device as an attachment to a hand-held motorized toothbrush handle equipped with a motor from which projects and output shaft. Depending upon the model, the gear train assembly may be modified to convert longitudinal stroking motion of the shaft or oscillatory motion into uni-directional rotating motion to rotate the take-up spool in one direction only.

58 Claims, 15 Drawing Sheets

U.S. PATENT DOCUMENTS

| | | | |
|---|---|---|---|
| 4,586,521 | 5/1986 | Urso | 132/322 |
| 4,605,025 | 8/1986 | McSpadden . | |
| 4,706,695 | 11/1987 | Urso . | |
| 4,756,202 | 7/1988 | Kawamoto . | |
| 4,830,032 | 5/1989 | Jousson . | |
| 4,883,080 | 11/1989 | Lang . | |
| 5,016,660 | 5/1991 | Boggs . | |
| 5,033,150 | 7/1991 | Gross et al. . | |
| 5,038,806 | 8/1991 | Ewald . | |
| 5,085,236 | 2/1992 | Odneal et al. . | |
| 5,094,256 | 3/1992 | Barth . | |
| 5,176,157 | 1/1993 | Mazza . | |
| 5,183,064 | 2/1993 | Barth . | |
| 5,183,065 | 2/1993 | Mason . | |
| 5,184,632 | 2/1993 | Gross et al. . | |
| 5,186,191 | 2/1993 | Loubier . | |
| 5,188,133 | 2/1993 | Romanus | 132/322 |
| 5,207,773 | 5/1993 | Henderson . | |
| 5,224,500 | 7/1993 | Stella . | |
| 5,269,331 | 12/1993 | Tanriverdi . | |

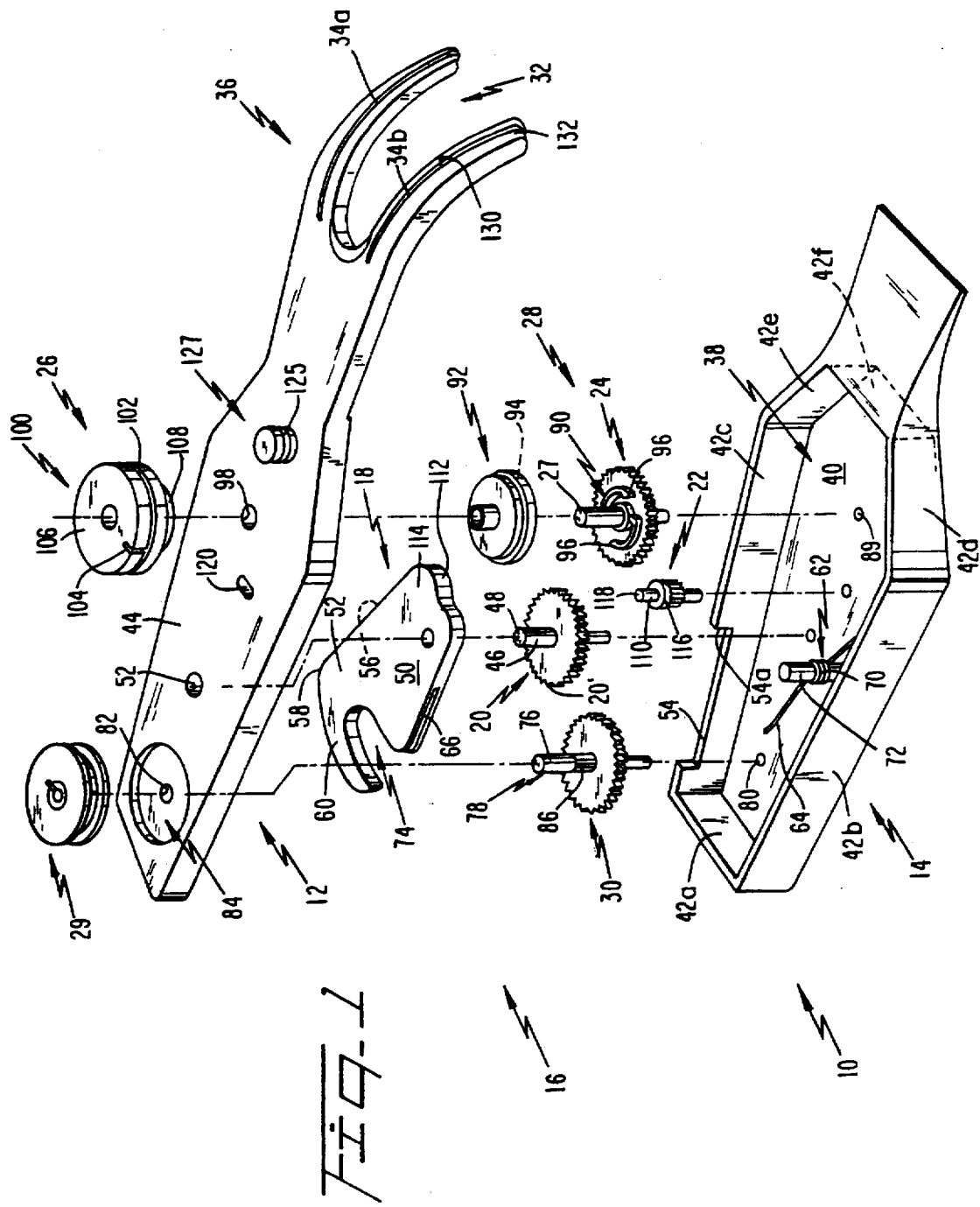

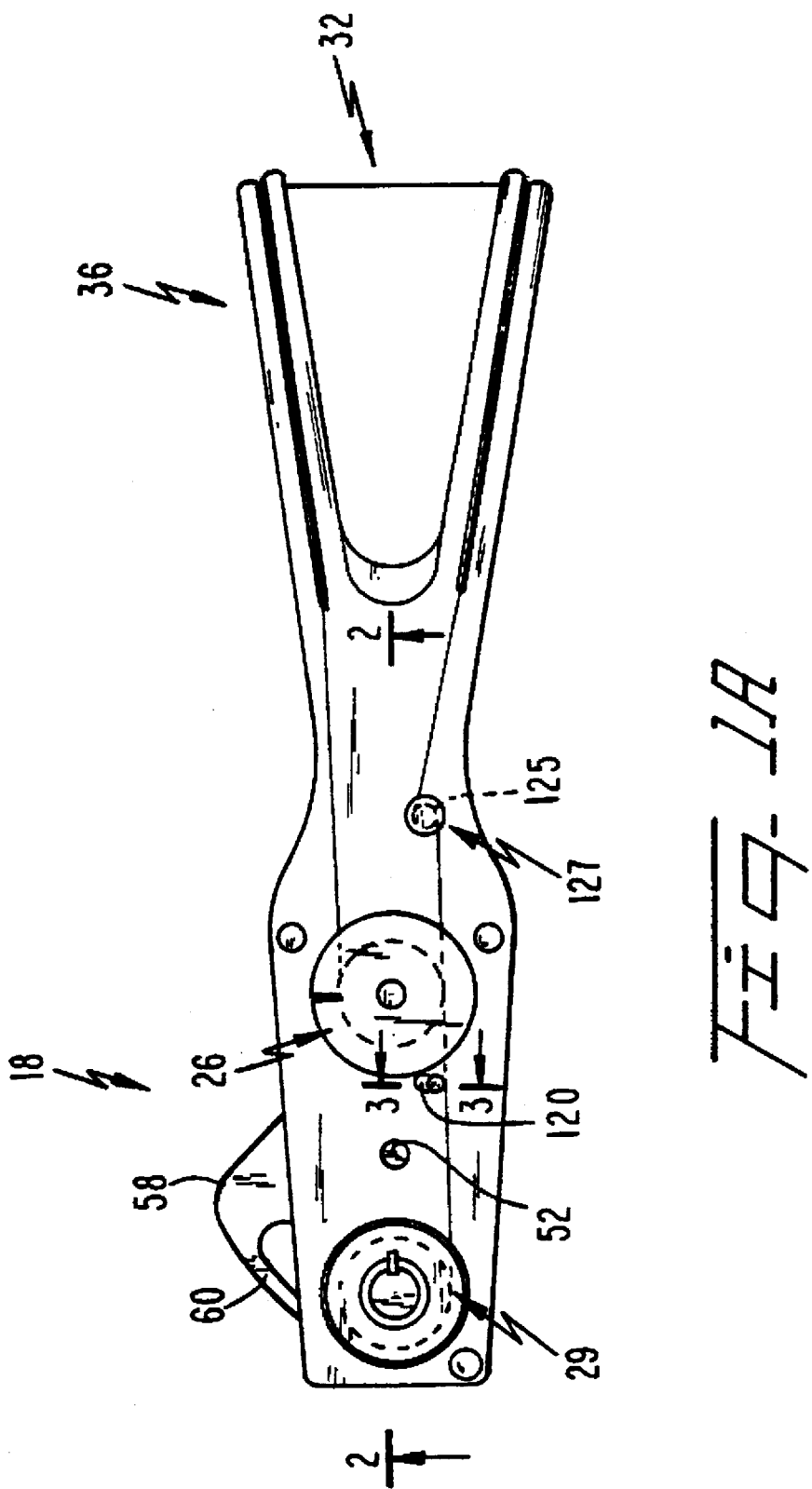

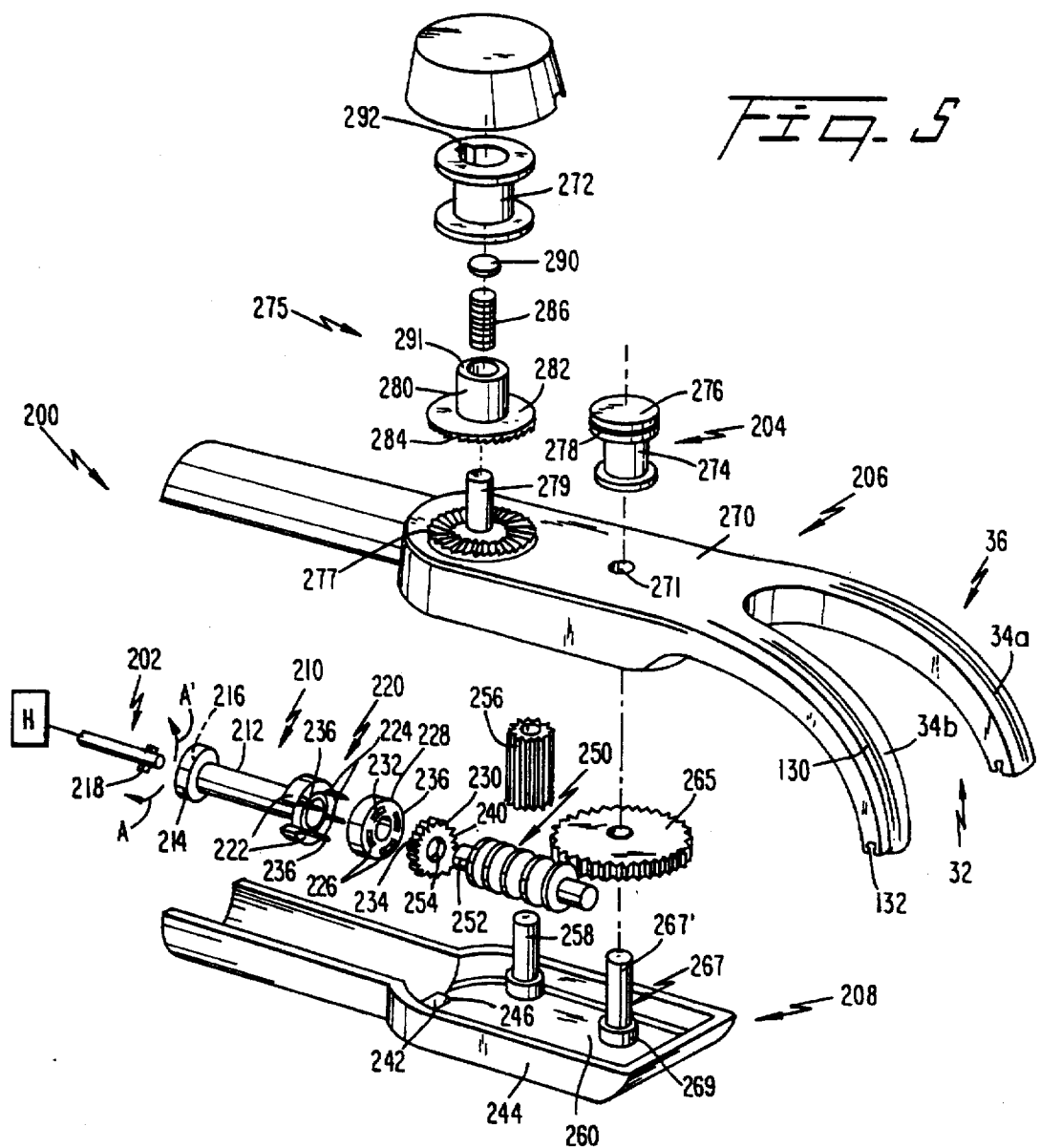

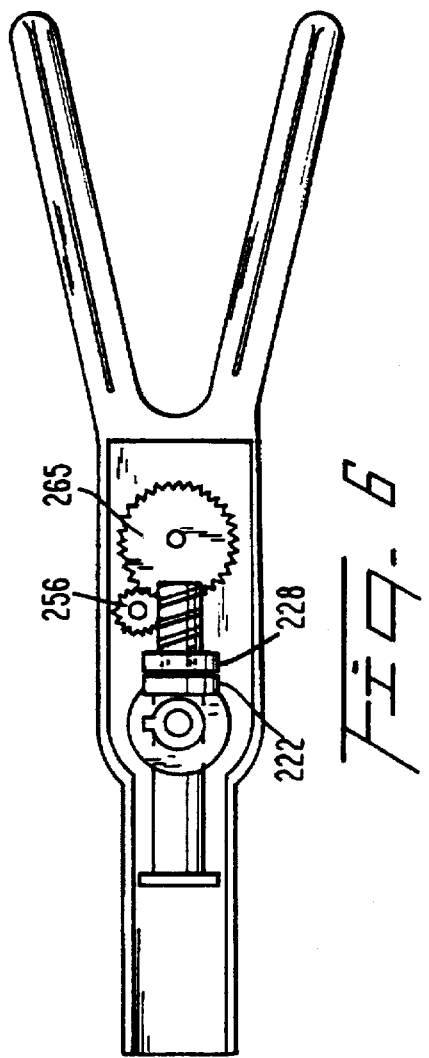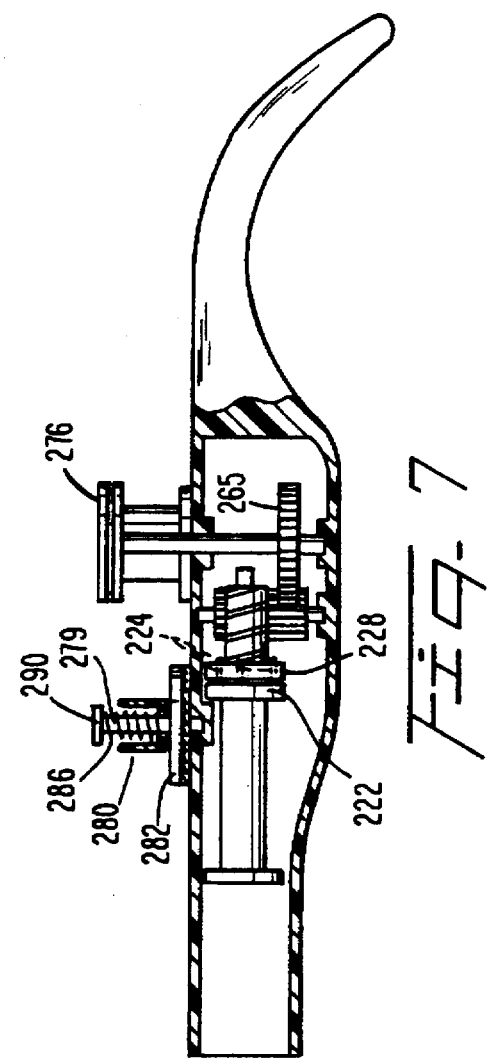

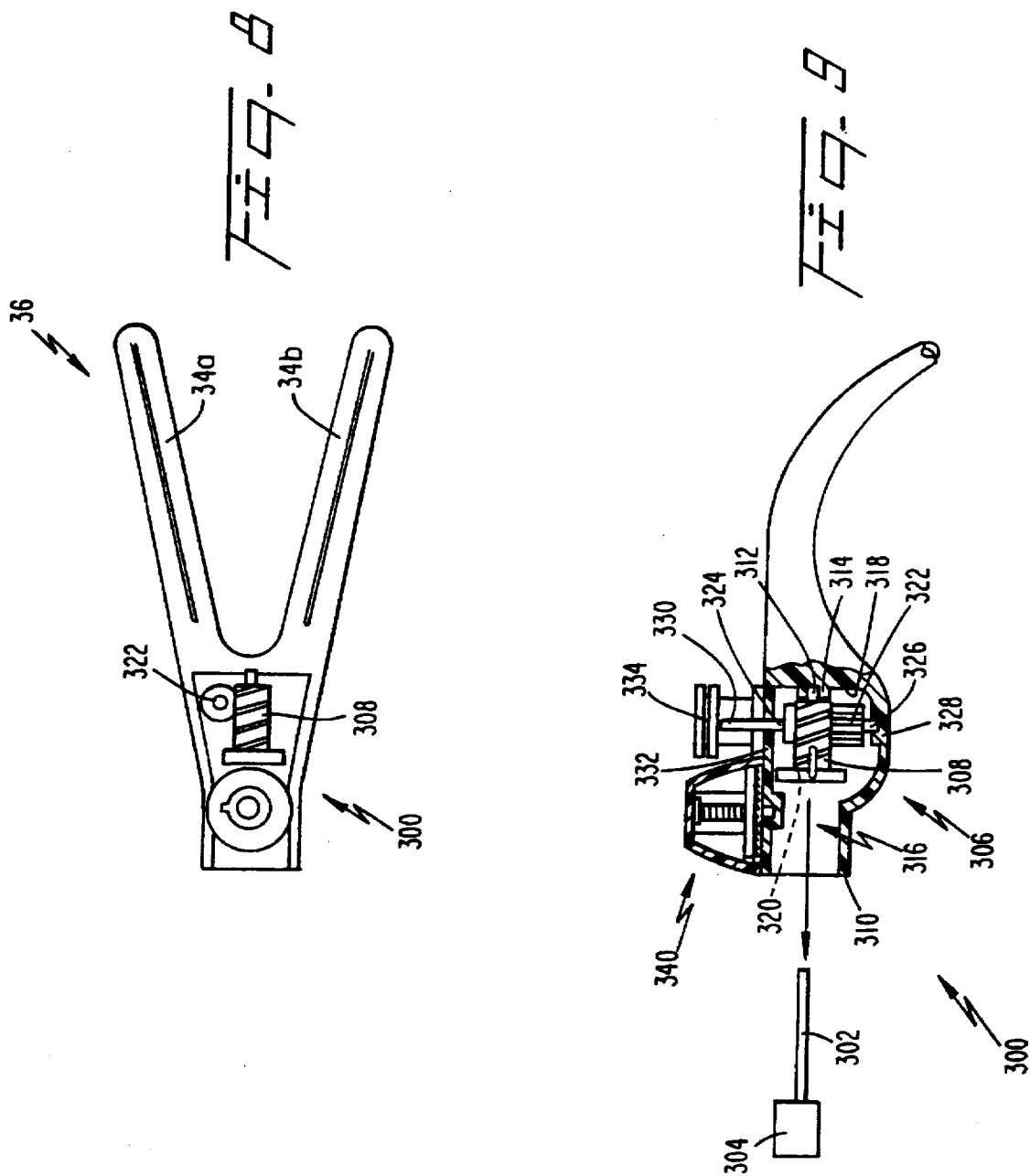

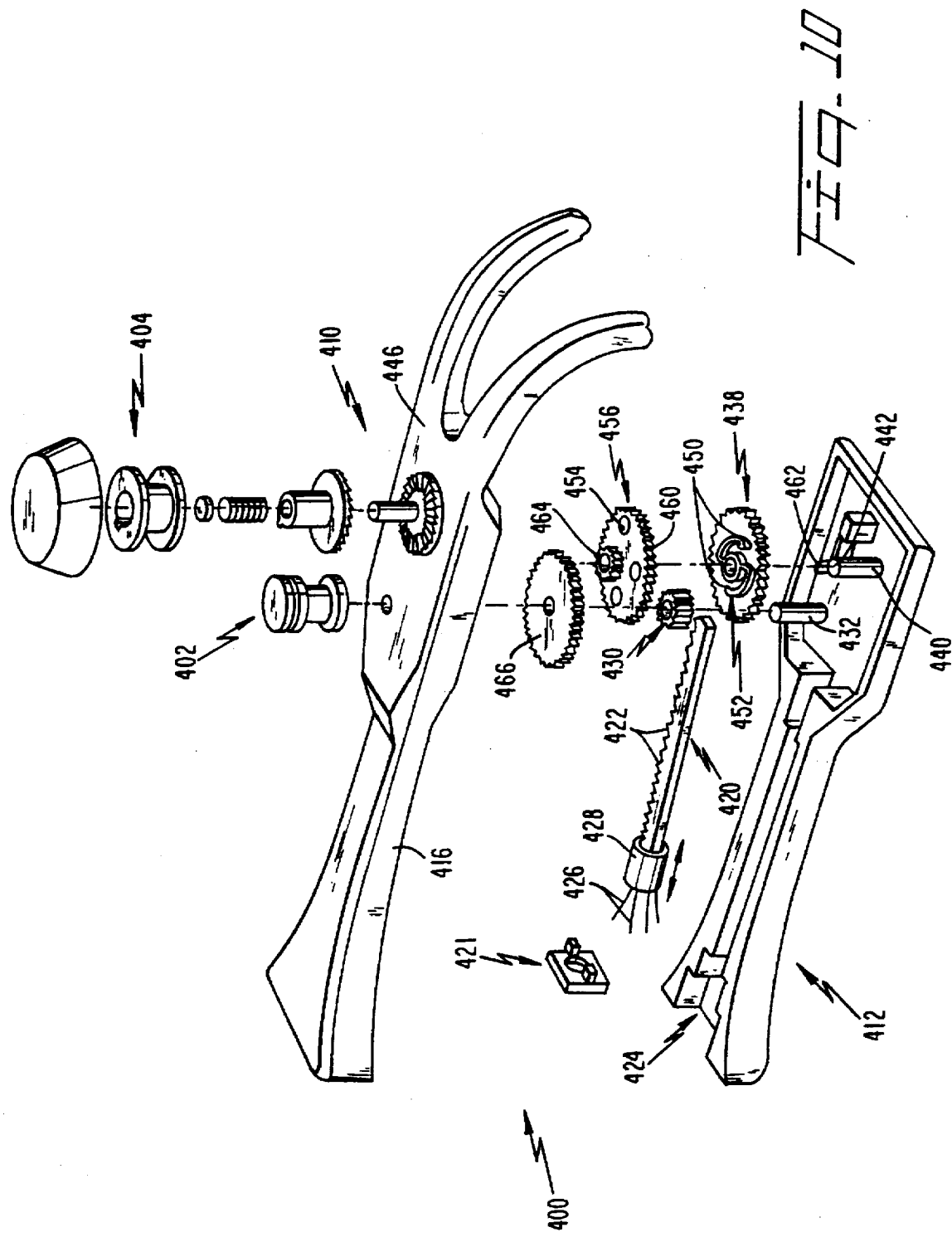

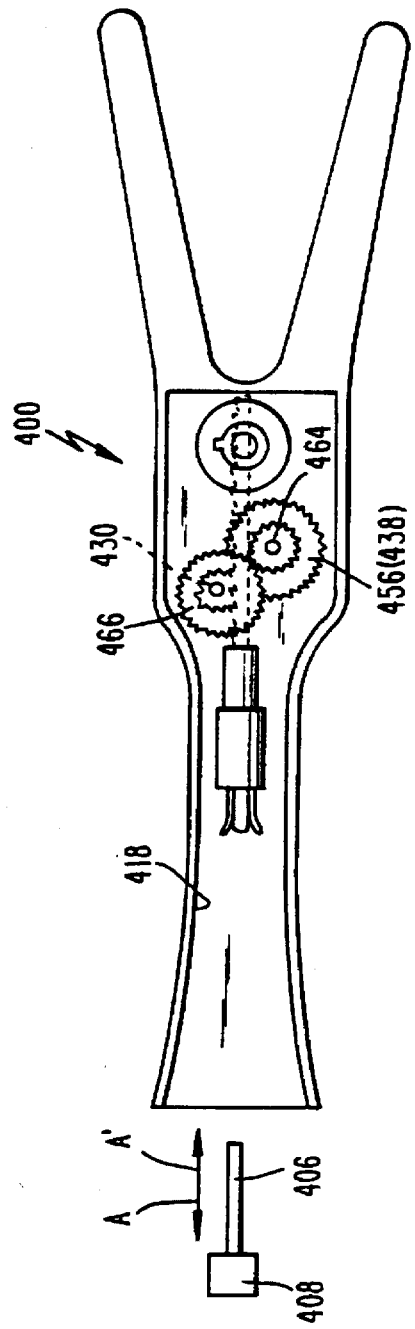
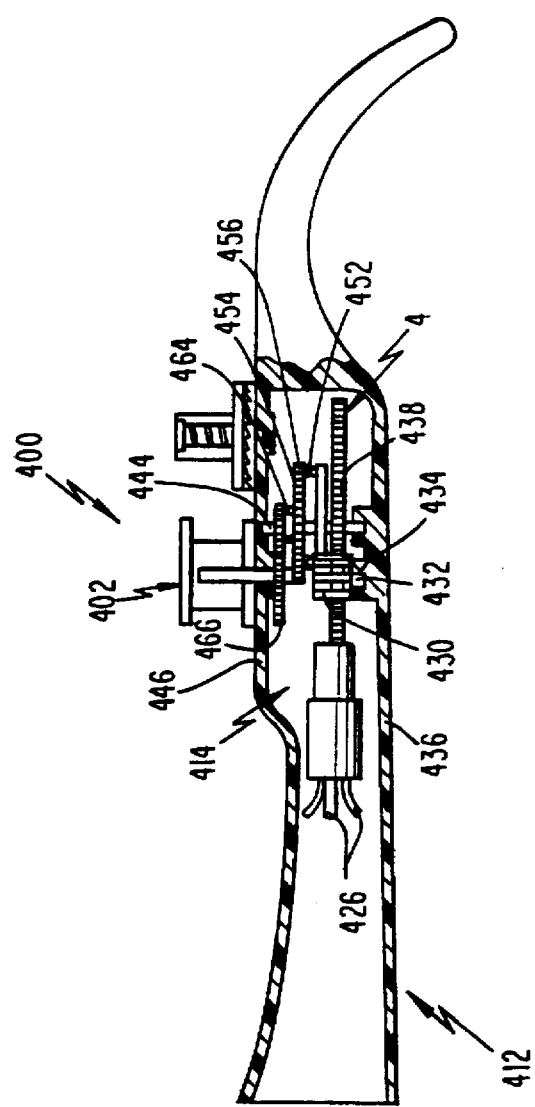

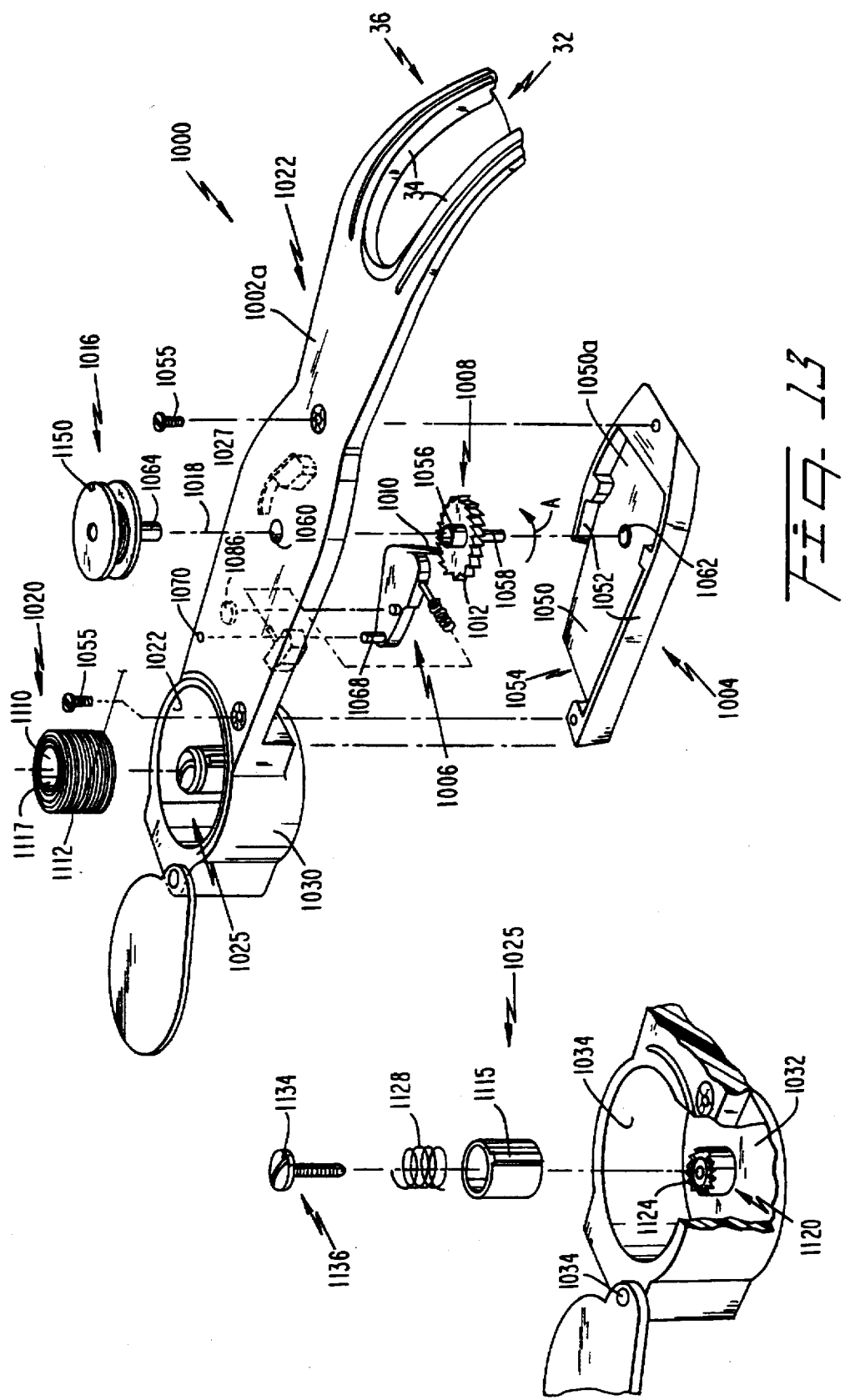

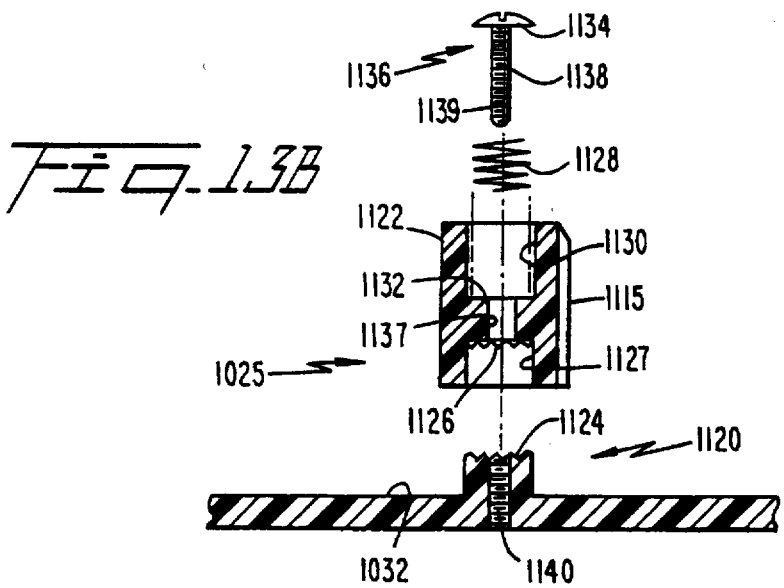
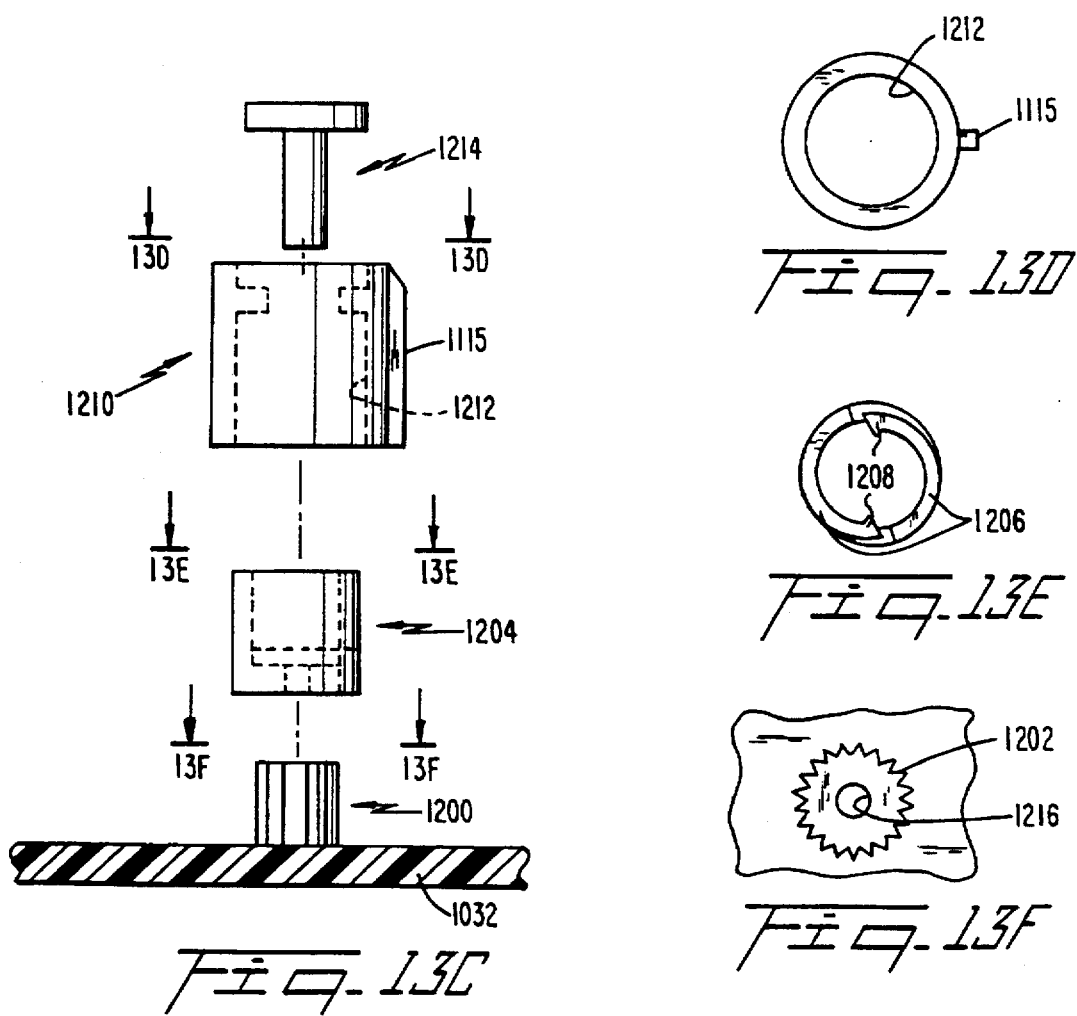

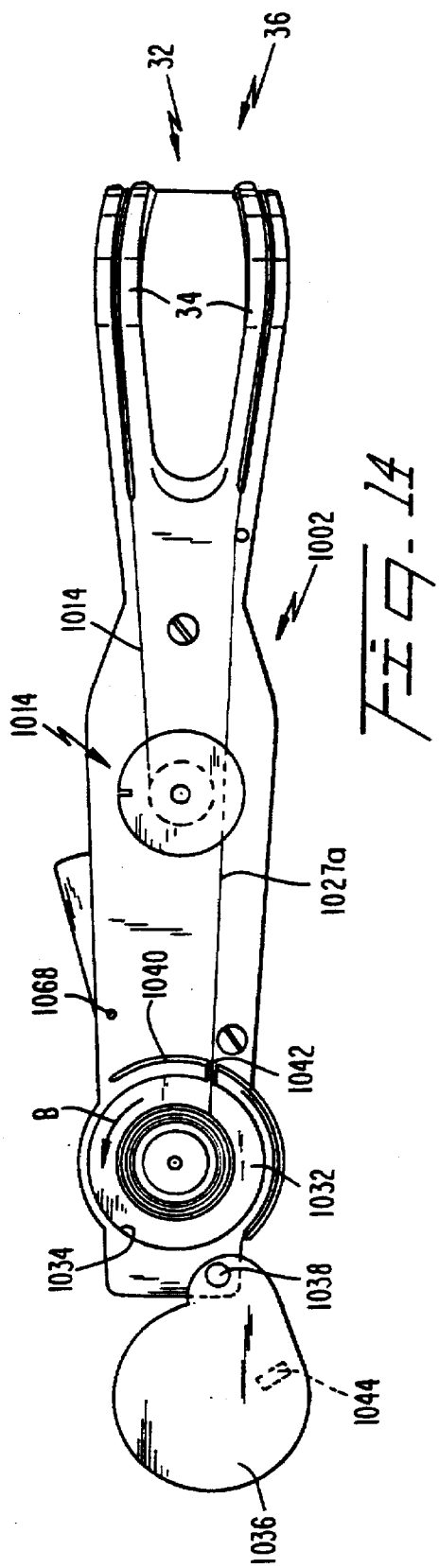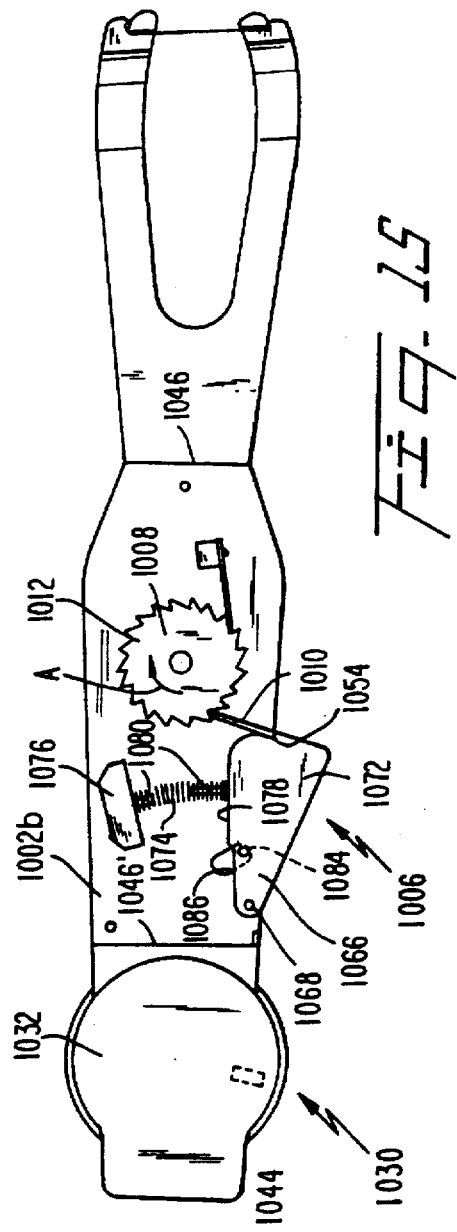

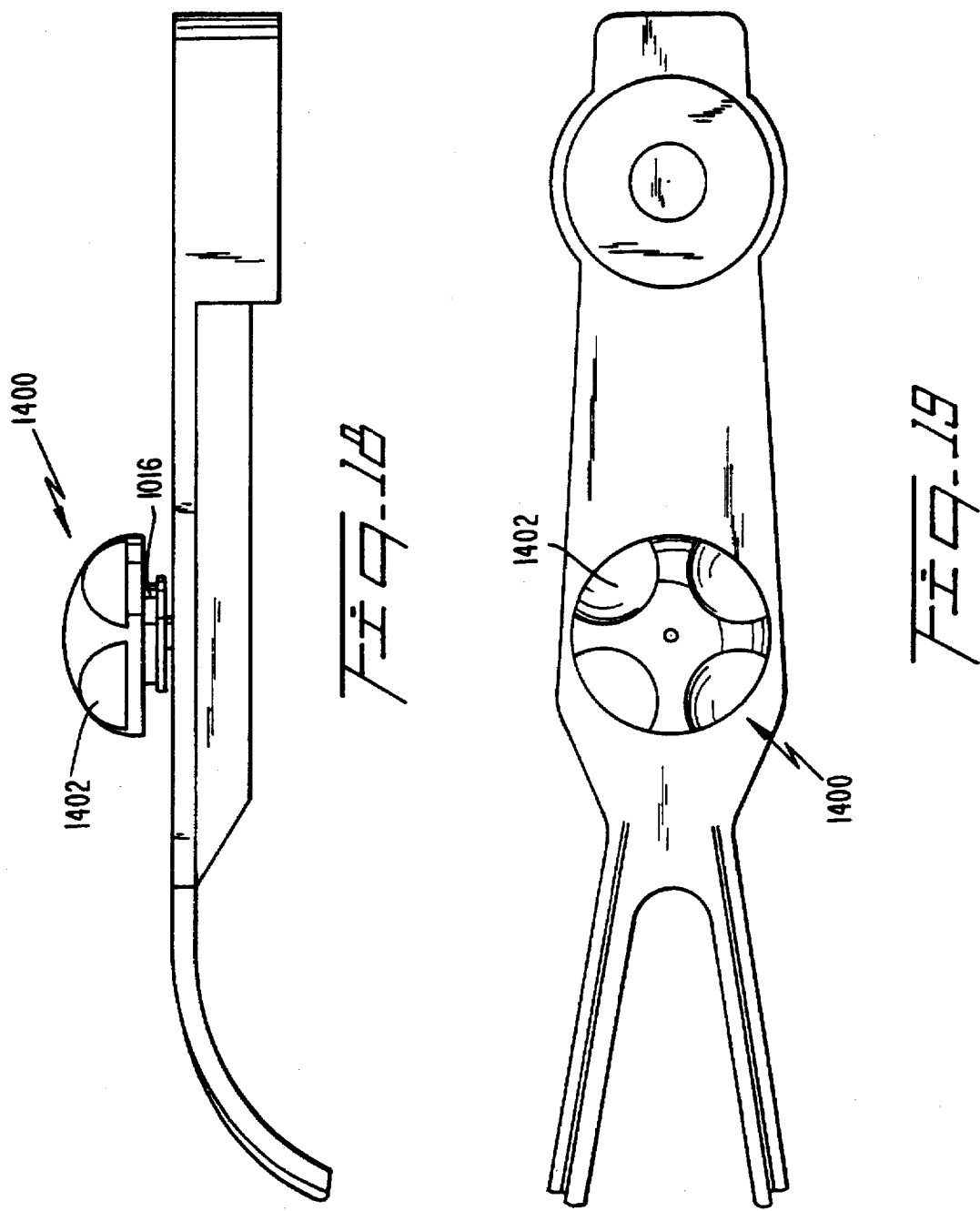

FLOSSING EQUIPMENT AND METHOD OF OPERATION

RELATED APPLICATIONS

This application is a continuation of application Ser. No. 08/267,939 filed Jul. 6, 1994, now abandoned which is a continuation-in-part of U.S. application Ser. No. 08/101,071, filed Aug. 3, 1993, now abandoned, and entitled "Flossing Equipment and Method of Operation."

TECHNICAL FIELD

The present invention relates generally to tooth flossing and, more particularly, to manual floss holders and power-driven floss holders which are attachable to automatic toothbrushes to be driven by the toothbrush motor for avoidance of periodontal diseases.

BACKGROUND ART

Flossing is the only effective method for cleaning between teeth to remove plaque buildup which is the primary causative agent of gingivitis, periodontitis, and tooth decay. The most commonly used method of flossing is to strip a large piece of floss off a dispenser, about one and one half to two feet, wrap it around one's fingers, and to then work an exposed piece of floss between the fingers of both hands up and down against the tooth surfaces defining the interproximal spaces between the teeth. Ideally, a freshly-exposed piece of floss is used for each interproximal space. Otherwise, continued use of the same exposed piece will likely result in transference of plaque and bacteria from one interproximal space to another.

For optimal results, the foregoing flossing procedure should be performed daily. However, only the most conscientious individuals adhere to such a strict schedule. This is because flossing is generally regarded as an unpleasant experience since there are a number of problems which occur during flossing which result in a failure to floss daily. One such problem, for example, is that it can be difficult and painful for the individual to wrap the floss tightly enough around the fingers to maintain the needed tension, and then to unwrap and rewrap the used piece to expose a fresh piece to floss the next interproximal space. It is also unpleasant to handle the wet, odorous, used floss and to wrap such material about the fingers of the hands. Additionally, gagging may occur during flossing and it can be painful to hold one's mouth open long enough and wide enough to floss every tooth, particularly rearwardly located teeth. Furthermore, it is often difficult to work with fingers from both hands in the mouth and the force applied to get the floss between the teeth can be excessive. Often, the floss snaps into the gum causing it to bleed. Furthermore, although floss is relatively inexpensive, quite a bit is used in a single cleaning and there is considerable waste, considering that the end portions of the floss are not used for cleaning but merely to be wrapped around each hand to provide the necessary anchoring for proper tension.

A number of dental flossing devices have been proposed for commercialization or are commercially available for the purpose of avoiding the use of one's fingers to position the floss correctly. For various reasons, most of these devices, if not all, are not widely accepted or practical and have not resulted in the increased regularity of flossing among the general population. Some of these devices, for example, are motor-driven and are provided with take-up and supply reel mechanisms which try to impart oscillation to the floss so that the floss moves back and forth to enhance flossing during use. One of the problems associated with these types of powered flossers is that the motors usually are not powerful enough to maintain oscillation as soon as the user attempts to thread the exposed piece of floss through a tight contact into an interproximal space between teeth. Oscillation would therefore stop and often the floss in the circuit would break, requiring rethreading.

Another problem associated with those powered flossers of which I am aware that impart oscillatory motion to the floss circuit during use is that such oscillation results in a sawing motion which can cut the individual's gums if improperly used.

Still another problem associated with the powered and manual flossers of which I am aware is the inability of the flosser to impart sufficient tension to the exposed piece of floss during the flossing operation. To be of practical use, a mechanical or powered flosser must have a flossing circuit whereby a high degree of tension is maintained against the exposed piece of floss during use, such tension being sufficient to enable the exposed floss to be threaded through a tight contact into each interproximal space. Numerous prior art flossers of which I am aware utilize a take-up spool for receiving used floss and a supply spool for supplying fresh floss into a part of the flossing circuit which is exposed for placement in the individual's mouth. Not only do these flossers fail to provide sufficient tension, most if not all rely upon structures wherein the take-up spool is located within a housing. This is extremely unhygienic, contaminates the flosser both inside and out, and creates an odorous situation.

Other problems associated with powered flossers of which I am aware is that the mechanisms tend to be complicated. If the floss in the circuit breaks, as normally occurs each time an individual flosses, it is virtually impossible for the flosser to rethread the floss onto the take-up spool.

Still other flossers of which I am aware rely upon a jet of water. However, the use of a water jet has been classically shown to be ineffective as a flossing substitute and only works on the outsides of the teeth and not interproximally, which is the area most vulnerable to decay and periodontal disease or bone loss.

It is accordingly one object of the present invention to provide a dental flossing device which is easy to use and easy to rethread in the event of floss breakage.

Another object is to locate a take-up supply spool for spent floss in an external position on the device to improve hygiene.

Still another object is to provide a manually operated flossing device which is both easy to use and capable of maintaining a high degree of tension to enable proper flossing usage.

Still another object is to provide a mechanically activated flossing attachment which may be easily attached to existing motorized hand-held toothbrushes for easy conversion to flossing usage.

DISCLOSURE OF THE INVENTION

A flossing device to facilitate the insertion of floss between teeth comprises, in accordance with the present invention, a housing including a forked extension defining a pair of prongs with grooves for guiding the floss in a circuit which spans a space between the prongs. A floss supply spool is rotatably mounted to the housing. A floss take-up spool is also rotatably mounted to the housing. The take-up spool is advantageously located outside the housing for hygienic reasons. A gear train assembly is disposed within the housing for rotating the take-up spool in a winding direction to receive used floss from between the prongs. An actuating mechanism is provided for actuating the gear train assembly to rotate the take-up spool. The gear train assembly is arranged to lock up and prevent reverse rotation of at least one of the take-up spool or supply spool. A ratchet mechanism connected to at least one of the other of the take-up or supply spool cooperates with the locked gear train assembly to tension the floss during periods when the actuating mechanism is deactivated.

In accordance with a preferred feature of this invention, the flossing circuit is located exclusively outside the housing. However, it is within the scope of this invention to locate the floss supply within the housing.

In accordance with various disclosed embodiments of this invention, the flossing device may be in the form of an attachment to a hand-held motorized toothbrush handle equipped with a motor from which projects and output shaft which functions as that actuating mechanism. The housing is further formed with a rear open end to receive a rear forward end of the toothbrush handle in connecting engagement with the output shaft extending into the housing. Means are provided in the housing for connecting the output shaft to the gear train assembly.

According to one embodiment of a mechanically activated flossing attachment, the output shaft of the commercially available toothbrush handle oscillates in opposite rotational directions through predetermined arcuate intervals (e.g., 60°). The connecting means includes a connector engageable at one thereof with the output shaft. The other end of the connector includes at least a pair of axially extending fingers projecting forward from the connector. A lost motion transmission disk contains plural spaced circumferential slots in axial alignment with the fingers respectively received in two of the slots. Rotational movement of the connector in one of the oscillatory directions is operable to cause driving contact of the fingers within a selected pair of slots to rotate the disk in one rotational direction. Rotational movement of the fingers in the opposite direction by the reversely rotating output shaft causes the fingers to rotate out of the slots into a pair of circumferentially next adjacent slots without rotating the lost motion transmission disk. Renewed motion of the disk in said one rotational direction occurs upon a change in movement of the connector through the shaft in said one rotational direction. The gear train includes an input gear connected to the disk for rotary motion only in said one rotational direction.

Still with reference to this embodiment, a ratchet tooth is fixed to the housing and a series of projections are formed on a portion co-rotatable with the disk. The ratchet tooth includes a first surface contactable with the projections to permit the projections to slide therepast in said one rotational direction. The tooth includes a second surface lockable against one other projections moving in the opposite rotational direction as a result of frictional contact between the fingers with the disk to thereby prevent reverse rotation of the input gear.

The input gear is preferably a worm gear and it is in meshing engagement with a speed reduction gear. A take-up spool drive gear in turn meshes with the speed reduction gear. The drive gear is mounted on a support shaft projecting through the housing to the exterior thereof to support the floss take-up spool co-rotatably mounted thereon. In this embodiment, the take-up spool is advantageously locked against rotation by the gear train assembly during non-rotation of the output shaft, i.e., when the motor is deactivated.

The take-up spool support shaft projects upward from the bottom wall of the housing substantially parallel to a second shaft supporting the speed reduction gear. The shafts defining the axes of rotation for these respective gears are preferably perpendicular to and offset from the worm axis of rotation. The worm is preferably coaxial with the output shaft.

The floss supply spool is driven in an unwinding rotational direction via rotation of the take-up spool only. In this embodiment, the ratchet mechanism is connected to the supply spool. The ratchet mechanism preferably comprises a first set of upward facing fixed teeth formed on one of the housing walls. A second set of downward facing teeth contact the first set. A hub projects upward from the second set for co-rotation therewith. A compression spring is mounted to the hub for urging the second set against the first set. The floss supply spool is mounted to the hub for co-rotation therewith. With this arrangement, rotation of the supply spool in the unwinding direction occurs against the resistance of the spring biased first and second tooth sets. This resistance is yieldable against rotation of the take-up spool during actuation of the device but cooperates with the locked take-up spool during period of the deactivation to thereby tension the floss circuit to a predetermined extent during flossing.

The first tooth set is preferably formed in a circular pattern about a post projecting upward from the housing wall at the center of the tooth array. The post projects upward through the hub through a bottom annular wall therein. A lower end of the spring is seated on the annular wall and extends upwardly around the post. Means engageable with the upper end of the post defines an upper spring seat for compressing the spring.

The second tooth set is also preferably arranged in a circular pattern in the lower surface of a disk from which the hub projects upwardly. Key means provided between the hub and supply spool is a preferred mode for rapidly detachably mounting the spool to the hub.

The take-up spool is preferably formed with a smaller diameter portion projecting downwardly towards the housing from a larger diameter cylindrical portion. The larger diameter portion is formed with an annular groove which is adapted to capture a free end of the floss to define one end of the flossing circuit.

In accordance with another mechanically activated flossing attachment according to the present invention, which is adapted to mate with a toothbrush handle wherein the motorized output shaft already rotates in one direction only, the gear train may be simplified. Therein, the input gear is a worm having an axis of rotation in coaxial alignment with the output shaft which is received directly in a rear portion of the worm. A speed reduction gear meshes with the worm and is mounted within the housing for co-rotation on a shaft projecting upwardly through the housing top wall to directly support the take-up spool to rotate the same. The take-up spool and feed spool assemblies, including the ratchet mechanism, may be identical to that described in the first mechanically activated embodiment.

In accordance with a third mechanically activated flossing attachment embodiment, it is adapted to be used with a motorized toothbrush handle wherein the output shaft reciprocates in longitudinal strokes along its shaft axis. Therein, the attachment housing includes a rack gear formed with rack teeth extending in coaxial alignment with the output shaft. Plural flexible fingers project rearwardly from the rack gear and are operable to receive and wrap around the forward end of the output shaft. Slidable clip means is longitudinally moveable to slide over the flexible fingers and press them against the output shaft forward end in clamping contact therewith to provide a secure connection.

In this third embodiment, the gear train assembly includes the rack gear and a pinion mounted in the housing in meshing contact with the rack gear teeth for oscillatory rotation thereby. A second gear is mounted in the housing and has an axis of rotation parallel to the pinion gear in meshing contact therewith. The second gear thereby also oscillates in opposite rotational directions. At least a pair of fingers project upwardly from the second gear to be received in a respective pair of circumferentially spaced slots formed within a lost motion transmission disk coaxially mounted above the second gear. These fingers engage end walls of the associated slots to drive the lost motion transmission disk in one direction only corresponding to movement of the rack gear in one of its strokes. Movement of the rack gear in its opposite stroke causes the fingers to rotate relatively to the slots, and out of the slots, to engage circumferentially adjacent slots to thereby rotate the lost motion transmission disk again upon renewed movement of the rack gear in the desired longitudinal stroke. This is how reciprocating motion is converted into uni-directional rotary motion within this embodiment.

A ratchet tooth is fixed to the housing and a series of projections are formed on the periphery of the transmission disk. The ratchet tooth includes a first surface contactable with these projections to permit them to slide therepast in said one rotational direction. The tooth includes a second surface lockable against one of the projections moving in the opposite rotational direction as a result of frictional contact between the fingers with the disk to thereby prevent reverse rotation of an input gear associated with the disk. This input gear is in meshing contact with a take-up spool drive gear co-rotatable to rotate the take-up spool in the winding direction.

In accordance with yet another embodiment of the invention, the flossing device is formed as a manually held, trigger operated unit. To that end, the actuating mechanism includes a manually depressible trigger and the gear train assembly located between upper and lower housings includes an input gear rotated by the trigger and a take-up spool drive gear mounted for co-rotation with the take-up spool. A transfer gear meshing with the input gear is operable to rotate the take-up spool drive gear during depressing of the trigger. A supply spool drive gear driven by the input gear is mounted for co-rotation with the supply spool to thereby rotate it in an unwinding direction during trigger actuation. Preferably, the supply gear is permanently meshed with the input gear and is thereby locked against rotational movement by the input gear when the trigger is not being depressed.

In a preferred embodiment of a manually held, trigger operated unit, a flossing device to facilitate the insertion of floss between teeth comprises a housing including a forked extension extending from the housing and having a pair of prongs with grooves for guiding the floss in the circuit which spans a space between the prongs. A floss supply spool and a floss take-up spool are respectively rotatably mounted to the housing. An actuating mechanism rotates the take-up spool to advance floss within the floss circuit. A first tensioning mechanism is connected to the floss take-up spool to tension the floss during periods when the actuating mechanism is de-activated. A second tensioning mechanism is connected to the supply spool to cooperate with the first mechanism to tension the floss during periods when the actuating mechanism is de-activated.

In the first manual embodiment, during release of the depressed trigger, the input gear is operable to reversely rotate the supply gear through a predetermined arcuate interval. This has the advantageous effect of removing slack from the floss circuit in cooperation with the take-up spool which is locked against reverse rotation by a ratchet mechanism. The ratchet mechanism includes a first ratchet member mounted on the take-up spool supply shaft for co-rotation therewith in the winding direction. A second ratchet member is provided with a set of annular inwardly extending teeth fixably mounted to the housing about the take-up spool shaft. The first ratchet member extends within the second member and is operable to lockingly engage the annular teeth during reverse rotation of the take-up spool to prevent the occurrence of the reverse rotation. During normal rotation, however, the ratchet member slides past the annular teeth.

In accordance with another feature of this invention, the transfer gear of the first embodiment is mounted on a tiltable shaft moveable between first and second positions as a result of meshing contact with the input gear. When the trigger is in its deactivated position, the transfer gear is out of meshing contact with the take-up spool gear. Depressing the trigger causes the rotating input gear meshing with the transfer gear to index the latter into meshing contact with the take-up spool drive gear as the transfer gear support shaft is moved from its first position into a second tilted position. During this movement of the shaft from the first to the second position, the supply spool gear does not rotate since the input gear is formed without teeth along a predetermined arcuate interval which initially contacts the supply spool gear during initial depressing of the trigger. After the transfer gear begins to mesh with the take-up spool gear, the toothed portion of the input gear now meshes with the supply gear to rotate the supply spool in the unwinding direction simultaneous with rotation of the take-up spool in its take-up direction. Return movement of the trigger during release thereof is operable to reversely rotate the input gear which releases the transfer gear from the take-up spool drive gear and causes the transfer gear support shaft to tilt back into its first position.

A method of flossing with a flossing device which is attachable to a hand-held motorized toothbrush handle equipped with a motor from which projects an output shaft is also disclosed. The flossing device comprises a housing provided with a take-up spool and a supply spool between which floss extends in a floss circuit. The method comprises the steps of attaching the housing to the toothbrush handle so that the output shaft thereof extends into the housing in driving contact with an actuating mechanism which rotates the take-up spool during periods of actuation. Flossing between a pair of teeth by inserting a flossing location of the flossing circuit into the mouth, however, occurs without operating the motor so that the floss in the flossing circuit is stationary during flossing. The flossing location is removed from between the said pair of teeth. After removal, the motor is activated to actuate the actuating mechanism to rotate the take-up spool and advance the spent floss from the flossing location which allows fresh floss to move into the flossing location. The motor is then deactivated and the flossing location is reinserted into the mouth to clean another pair of teeth. These steps are repeated until flossing is complete.

In a broad context, the invention with respect to the manually held, trigger operated flossing units is concerned with a method of flossing comprising the steps of depressing the trigger of a flossing device to advance floss in a flossing circuit of the device by an incremental amount. The trigger is then released. Flossing then occurs by inserting a portion of the device into the user's mouth, said portion including exposed floss in a tension circuit. The foregoing steps are then repeated.

The above and still further objects, features and advantages of the present invention will become apparent upon consideration of the following detailed description of a specific embodiment thereof, especially when taken in conjunction with the accompanying drawings.

BRIEF DESCRIPTION OF DRAWINGS

FIG. 1 is an exploded perspective view of a manually hand-held flosser in accordance with the present invention;

FIG. 1A is a top view of the flosser of FIG. 1;

FIG. 5 is an exploded perspective view of a first embodiment of a mechanically actuated flossing attachment adapted to be detachably mounted to an electric toothbrush having a motorized oscillating output shaft;

FIG. 6 is a top, partly sectional view of the FIG. 5 embodiment;

FIG. 7 is a side elevational view of the FIG. 5 embodiment;

FIG. 8 is a top plan view of a second embodiment of a mechanically actuated flossing attachment adapted to be detachably mounted to an electric toothbrush having a motorized output shaft rotating in one direction only;

FIG. 9 is a side elevational view of the FIG. 8 embodiment;

FIG. 10 is an exploded perspective view of a third embodiment of a mechanically activated flossing attachment adapted to be detachably mounted to an electric toothbrush having a motorized output shaft which moves longitudinally in reciprocating strokes;

FIG. 11 is a top plan view of the FIG. 10 embodiment;

FIG. 12 is a side sectional view of the FIG. 10 embodiment;

FIG. 13 is an exploded perspective view of a preferred embodiment of a manually held flosser in accordance with the present invention;

FIG. 13A is an exploded perspective view of a floss supply compartment in the hand-held flosser of FIG. 13;

FIG. 13B is an exploded perspective sectional view of the floss supply spool mounting assembly in accordance with the preferred embodiment;

FIG. 13C is an exploded sectional view of an alternative embodiment of a floss supply spool mounting assembly;

FIG. 13D is a sectional view taken along the line 13D—13D of FIG. 13C;

FIG. 13E is a sectional view taken along the line 13E—13E of FIG. 13C;

FIG. 13F is a sectional view taken along the line 13F—13F of FIG. 13C;

FIG. 14 is a top plan view of the hand-held flosser of FIG. 13;

FIG. 15 is an interior plan view of the hand-held flosser of FIG. 13;

FIG. 18 is a side plan view of a further embodiment of the hand-held flosser of FIG. 13;

FIG. 19 is a top plan view of the hand-held flosser of FIG. 18;

Figure 2:
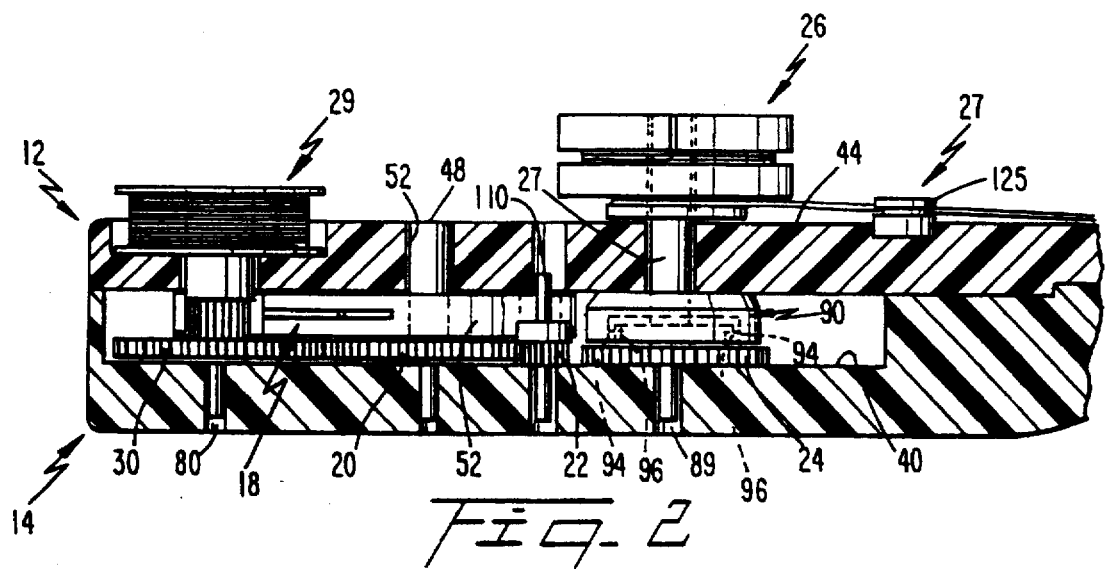
FIG. 2 is a sectional view taken along the line 1—1 and partly along line 3—3 of FIG. 1A to depict the operative relationships between the gear train assembly with the take-up spool.

BEST MODE FOR CARRYING OUT THE INVENTION MANUALLY ACTIVATED DENTAL FLOSSING DEVICE

FIG. 1 is an exploded perspective view of a manual dental flossing device 10 comprised of a handle formed from a top housing 12 and a bottom housing 14 containing a uniquely-arranged gear train, generally designated by reference numeral 16, which is operated by a spring-loaded trigger mechanism 18 protruding laterally from the bottom housing. Manually depressing the trigger mechanism 18 is operable to partially rotate an input gear 20, co-rotatably mounted to the trigger, which in turn counter-rotates a transfer gear 22 while indexing it into meshing contact with a take-up spool drive gear 24. The take-up spool drive gear 24 is rotatable with gear 22 in one direction only, i.e., to wind preferably-used floss onto a take-up spool 26 mounted on the same shaft 27 as gear 24, and is located advantageously above top housing 12. As this counter-clockwise winding action occurs during depressing of trigger 18, a floss-supply spool 29, also located atop housing 12, is simultaneously rotated counter-clockwise in an unwinding direction as a result of meshing contact between a floss-supply spool drive gear 30, mounted to rotate the supply spool, with the input gear 20, after the input gear has initially rotated to index the transfer gear into meshing contact with the take-up spool gear. In this manner, fresh floss is progressively advanced in a flossing circuit where it is stretched and tensioned across a space 32 formed between a pair of identical prongs 34 of a fork 36 which defines a forwardly-extending portion of the top housing 12. Release of the trigger mechanism 18 causes reverse rotation of the input gear 20 and the floss-supply drive spool drive gear 30 meshing therewith. This has the advantageous effect of also slightly reversely rotating the floss-supply spool 29 which removes slack in the floss-supply circuit and imparts a high degree of tension to the floss in space 32. Reverse rotation of the take-up spool 26 in an unwinding or clockwise direction is advantageously prevented by a one-way clutch mechanism 28, also mounted on take-up spool shaft 27.

More specifically, the bottom housing 14 in the preferred embodiment is formed with an upward-facing open cavity 38 defined by a bottom wall 40 and upwardly-projecting sides 42a, 42b, 42c, 42d, 42e and 42g. Gear train 16 is disposed within cavity 38 before being covered by the top housing 12 which is actually in the form of an elongated cover plate 44 extending rearwardly from the fork 36. Although not shown for the sake of simplicity, this plate 44 is formed with through-holes adapted to receive correspondingly-aligned posts projecting upwardly from bottom 40 along the inner surfaces of side walls 42a–42c to provide for releasable securement of the top plate to the bottom housing. Of course, screwed connections may be provided in place of or with these alignment post connections.

The trigger mechanism 18 is a substantially-flat, relatively thin plate-shaped member having a profiled side edge in plan view which is mounted in an intermediate portion of the gear train housing cavity 38 on a trigger pin 46 having a lower end rotatably supported in bottom wall 40. An upper end 48 of pin 46 projects upward from a center pivot or crank portion 50 of the trigger 18 to be rotatably received in a through hole 52 formed in the top cover plate 44 of housing 12. The input gear 20 is also mounted for co-rotation with trigger 18 on the same vertical pin 46 and extends horizontally in parallel relation with the bottom surface of the trigger plate adjacent the cavity bottom wall 40. The trigger pin 46 thus defines a common vertical axis of rotation for both the trigger plate and the input gear 20 co-rotatable therewith.

A distal portion 52 of the trigger mechanism 18 projects radially from the center portion 50 to protrude laterally outwardly from a slot 54 formed in an upper edge of one of the longitudinally-extending bottom cavity side walls 42c to define the manually-depressible trigger protruding laterally from the bottom housing 14. The forward extent of this distal trigger portion 52 is defined by an inclined surface 56 which extends outwardly and rearwardly from a point within the cavity 38, through the slot 54 to terminate at a point of intersection 58 outside the bottom housing 14 with an oppositely-inclined distal portion 60 of the trigger which projects rearwardly towards the back of the slot 54 to re-enter the cavity. The front surface 56 of the depressible trigger portion 52 is normally biased in a clockwise direction into contact with the front edge 54a of the slot 54 with a leaf spring 62 having a sprung wire portion 64 projecting into a slot 66 formed in a rearwardly-projecting part 68 of the trigger center portion 50 located aft of trigger pin 46 diametrically opposite the front surface 54. This sprung wire portion 64 extends rearwardly from a coiled spring portion 70 would around a stationary vertical support pin 72 projecting upwardly from the cavity bottom wall 40 at a location immediately adjacent an intermediate portion of the cavity side wall 42b opposite the slotted wall 42c. The forward vertical edge 54a of the slot 54 thus acts as a stop for the trigger portion 52 when it is spring-biased to its normally outwardly-protruding position.

The rearwardly extending distal portion 60 of the trigger 18 formed between the center pivot portion 50 and the manually depressible portion 52 is formed with a slot 74 which is provided to receive an intermediate portion 76 of the vertical floss supply spool mounting shaft 78 extending between the floss supply spool drive gear 30 (located elevationally below the trigger plate) and the bottom surface of the top cover plate 44. This slot 74 therefore provides clearance between the trigger plate, as it is manually depressed, and the floss supply spool mounting shaft 78 and gear 30 to result in a compact gear train arrangement.

A lower end (not shown) of the floss supply spool shaft 78 is rotatably received in a hole 80 formed in the cavity bottom 40. The intermediate portion 76 of the shaft 78 is a larger diameter portion rotatably received in a through hole 82 formed in the top cover plate 44. This larger diameter portion projects upwardly into a cylindrical recess 84 in the top plate upper surface 44 adapted to receive the floss supply spool 29. The upper end of this larger diameter shaft portion 76 is slotted at 86 to receive a key (not shown) for securing the floss supply spool 29 to the shaft 76 to ensure co-rotation therewith.

It will be appreciated that, as a result of this keyed connection, the floss supply spool 29 is easily detached from the upper end 78 of the supply spool shaft 76. This will advantageously allow for easy and rapid replacement of an empty floss supply spool with a fresh spool.

As mentioned, the input gear 20 is co-rotatably mounted to the trigger pin 46 which defines a vertical axis of rotation or pivot for both the trigger 18 and the input gear. This input gear 20 is co-elevational and in meshing contact with the floss supply spool drive gear 30 located immediately rearwardly adjacent thereto. The take-up spool drive gear 24 also extends in the same horizontal plane as the gears 20,30, immediately adjacent to the cavity bottom wall 40, and is spaced forwardly from the input gear 20. More specifically, the take-up gear 24 is co-rotatably mounted on the vertical take-up shaft assembly 27 having a lower end projecting below the gear 24 and which is rotatably received in a hole 89 formed in the cavity bottom wall 40. A portion of the shaft 27 projecting above the gear 24 is formed with a ratchet portion 90 co-rotatably mounted to the take-up shaft to allow for shaft rotational movement in the take-up direction only of the spool 26 as a result of engagement with annular ratchet portion 92 fixedly mounted to project from a lower surface of the top cover plate 44 into the cavity 38. This annular ratchet portion 92 is formed with a series of circumferentially arranged internal ratchet teeth 94 which are stationary and engage the teeth 96 of the rotatable ratchet portion 90 to lock up both the take-up spool 26 and take-up spool drive gear 24 to prevent undesirable reverse rotation thereof in an unwinding direction.

The upper end of the take-up spool mounting shaft 27 projects upwardly from the one-way ratcheted clutch mechanism 90 through a vertical through-hole 98 formed in the top cover plate 44. The take-up spool 26 is mounted to the upper end of this shaft 27. More specifically, the take-up spool 26 is formed with a large diameter upper cylindrical portion 100 formed with an annular groove 102 intersecting a vertical groove 104 communicating with the top surface 106 of the take-up spool. A smaller diameter portion 108 of the take-up spool 26 is formed beneath the larger diameter portion 100 and is also located above the top surface of the cover plate 44. When threading a fresh supply of floss to initially establish a floss supply circuit, the leading end of the fresh floss is preferably first wrapped for several turns into the annular groove 102 with the terminal end then being led into the vertical slot 104 (the remaining projecting floss end then being cut) to securely anchor the floss to the take-up spool 26. Optionally, the floss may also be wrapped around or stored on the small diameter portion 108.

Figure 3:
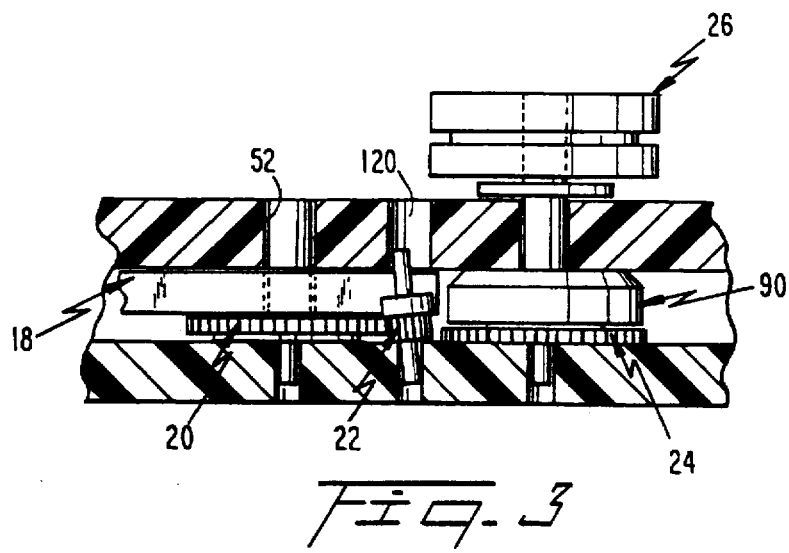
FIG. 3 is a partial sectional view taken along the line 3—3 of FIG. 1A depicting the location of a transfer gear when the trigger is deactivated.

In the preferred embodiment, it is the rotation of the take-up spool 26 in the winding (i.e., counter-clockwise) direction through the interaction of the input gear 20 and the transfer gear 22 meshing with take-up gear 24 which allows the user to selectively index the spent floss from the space 32, along the left-hand prong 34a and eventually onto the take-up spool 26. Since the input gear 20 advantageously performs the additional functions of tensioning the floss as a result of reversely rotating the supply spool gear 30 through a small arcuate interval, and thereby the supply spool 26 during spring loaded return of the trigger mechanism 18, and then remains in meshing contact with the supply gear to prevent the supply spool from rotating until the trigger is next depressed, it is important that the input gear be disengaged from the take-up spool drive gear 24 when the trigger is released. To achieve this object, the transfer gear 22, which is always in meshing contact with the input gear 20, is mounted on a vertically extending support pin 110 which is tiltable between first and second positions (in relation to a vertical axis) in and out of meshing contact with take-up gear 24. In the first position (FIG. 3), corresponding to the de-activated position of the trigger 18, the transfer gear 22 is biased out of meshing contact with the take-up spool drive gear 24. This biasing is achieved by means of a profiled cam surface 112 formed in a portion 114 of the trigger plate which projects forwardly from the center or pivot portion 50. This cam surface 112 is in co-elevational alignment with a small diameter cylindrical cam follower 116 which is mounted on the transfer gear mounting pin 110 above the transfer gear 22 for co-rotation therewith. The upper end 118 of this pin 110 projects above the cam follower 116 and is received in an elongated slotted opening 120 formed in the cover plate 44 of the top housing 12.

Figure 4:
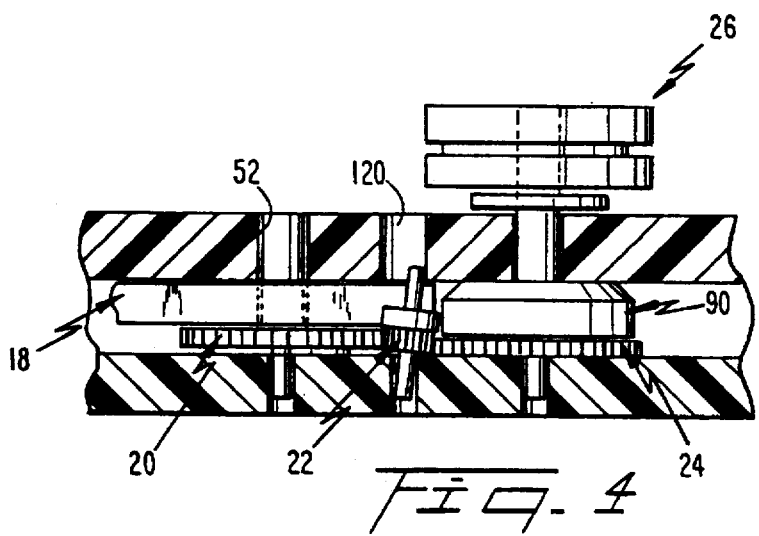
FIG. 4 is a view similar to FIG. 3 but of the transfer gear tilted into a position driving the take-up spool drive gear during trigger actuated floss advancement.

This unique de-clutchable transfer gear mechanism operates as follows. As the spring-loaded trigger 52 is depressed against the bias of spring 64, the cam surface 112 is retracted (rotated counter-clockwise) from the cam follower 116, with co-rotation of the input gear 20 immediately tilting the transfer gear support pin 110 from the first tilted position (FIG. 3) to a second tilted position (FIG. 4) where the transfer gear travels into meshing contact with the take-up spool drive gear 24. This action occurs since the upper end 118 of the transfer gear support pin 110 is allowed to travel through the elongate slot 120 in the top plate 44 to the second tilted position where the transfer gear is now in meshing contact with both the input gear 20 and the take-up spool drive gear 24 to transmit counter-clockwise or take-up rotation to the latter. After the trigger 52 has been manually depressed to sequentially index a fresh piece of floss across the space 32, the trigger is then released. As the input gear 20 reversely rotates, it is still and always in meshing contact with the transfer gear 22 and thereby immediately causes the upper end 118 of the transfer gear support pin 110 to travel back through the slot 120 from the second position to the first position where the pin is tilted away from the take-up spool supply gear 24. This has the effect of almost immediately disengaging the transfer gear 22 from the take-up spool drive gear 24. As the trigger 52 returns to its de-activated position, the input gear 20 continues to reversely rotate the floss supply spool drive gear 30 so as to tension the floss in the circuit. Tensioning resistance is meanwhile supplied at the take-up spool 26 through the one-way clutch mechanism 90,92. As the trigger mechanism 18 returns to its fully de-activated or home position under spring bias, the cam surface 112 once again engages the cam follower 116 to ensure that the transfer gear support pin 110 remains in its first tilted position away from the take-up spool drive gear 24 until manual depressing of the trigger next occurs.

The input gear 20 is formed with a smooth peripheral portion 20' of predetermined arcuate extent, devoid of gear teeth, which is positioned to prevent initial rotation of the supply spool gear 30 until the input gear has indexed the transfer gear 22 into initial contact with the take-up gear 24. It will be understood that the teeth on gear 20 preceding the smooth portion 20' are in meshing contact with the teeth on supply spool gear 30 when the trigger 18 is not depressed and therefore locks the supply spool against rotation. These immediately preceding teeth move out of meshing contact with the gear 30 as trigger 18 is initially depressed and smooth portion 20' slides past the supply spool teeth to delay rotation of the supply spool in the aforesaid manner. This prevents feeding of floss until the take-up spool gear 24 engages transfer gear 22 to co-rotate with the supply spool.

The manual dental flossing device 10 of the present invention possesses numerous advantages over prior art flossers of which we are aware. Locating the take-up spool 26 outside of the gear train housing 12,14, for example, advantageously avoids contamination within the housing by used floss and results in easy cleaning with water to prevent the occurrence of an unhygienic situation. The keyed mounting 86 of the supply spool 29 also outside the housing 12,14 advantageously allows an empty supply spool to be easily detached from its keyed shaft 76 to facilitate rapid replacement with a fresh supply spool.

Re-threading of the floss in the event of breakage or replacement to quickly reestablish the floss circuit is also easy. After manually unwinding a sufficient length of the floss from the supply spool 29, the floss is placed within a slotted opening 125 formed in the side of a cylindrical guide 127 mounted on the top cover plate 44 forwardly from the take-up spool 26 and on the supply side of the circuit. This slot 125 has the effect of spacing the fresh floss from the take-up spool 26 while aligning the fresh floss with an upwardly directed groove 130 extending along the length of the supply prong 34b of the fork 32 in the top surface thereof. This floss is then stretched across the space 32 between the prongs 34a,34b by being disposed within a pair of short, transversely extending slots 132 respectively formed in the front ends of the prongs. The floss is then threaded through an upwardly directed slot 130 formed in the top surface of the take-up prong 34a. The leading end of the floss is then wound onto the take-up spool 26 in the manner described above and any remaining portion of the leading end extending from the take-up spool can then be cut.

The feature of providing a one-way clutch on the take-up spool 26 advantageously prevents undesirable reverse or clockwise rotation in the unwinding direction. Furthermore, since the supply spool gear 30 is in constant mesh with the input gear 20 (except upon initial depressing of trigger 18 as noted above), this has the added advantage of preventing undesirable rotation of the supply spool in the unwinding or counter-clockwise direction unless the manual trigger 18 is intentionally depressed to feed the floss. That is, the supply spool gear 30 is positively locked against inadvertent or uncontrolled rotation when the trigger 18 is not being depressed, i.e., during flossing. Furthermore, since the depressed trigger 18 as it returns to its de-activated position under spring bias will also cause the input gear 20 to reversely co-rotate back to its initial position, this in turn imparts a slight degree of reverse rotation to the supply spool 29 which has the advantageous effect of tensioning the floss. This is made possible by the tilt sliding movement of the transfer gear 22 which is moved out of meshing contact with the take-up spool 24 gear in the manner described in detail above.

The material of which the flossing device 10 is made may include multiple plastics, nylon, polyester, other polymers, and combinations of the above. Aluminum, stainless steel, and other metals may also be used.

Mechanically Activated Dental Flossing Device

1. Braun Attachment

FIGS. 5-7 are illustrations of a mechanically activated dental flossing device 200 which is adapted to be activated by the output shaft 202 of a commercially available electric toothbrush handle H containing a motor which rapidly reversely rotates the output shaft in opposite directions A,A' through short arcuate intervals of approximately 60° when the motor in the hand-held unit is turned on. One such device having these output shaft characteristics is the Braun electric toothbrush handle, manufactured by Oral-B Company, a division of Gillette Company, Boston, Mass.

As will be seen more fully below, the mechanically activated dental flossing device 200 of this invention converts the oscillatory rotation of the electric toothbrush handle output shaft 202 into a uni-directional rotary motion to enable a take-up spool 204 in the flossing device to successively advance dental floss through the device in the unique manner described below. It is to be understood that the dental flossing device 200 of this invention is preferably not activated while the user is actively flossing between teeth. In accordance with a method of use of this invention, the floss in all the embodiments described herein is preferably only advanced between successive flossing operations. In other words, the floss which is stretched across the space 32 between the prongs 34a,34b of the fork 36 is preferably stationary in relation to the prongs during actual flossing.

The flossing attachment device 200 of this embodiment is comprised of a top housing 206 and a bottom housing 208 which may be screwed together in a manner obvious to one of ordinary skill in the art, or connected together with posts in the manner of the manually activated dental flossing device 10 described hereinabove. The attachment 200 itself has no motor of its own but is activated when linked to the oscillatory output shaft 202 in the electric toothbrush handle H such as in the Braun electric toothbrush. To that end, attachment 200 includes a connector 210 having a shaft portion 212 formed with a rear socket 214 having a notched depression 216 in a rear end face thereof, corresponding in cross-section to the protuberances 218 in the output shaft 202 in mating contact therewith. In this manner, oscillatory or back and forth rotating motion from the output shaft 202 is transmitted to a ratcheted socket 220 in the front end of the connector 210.

The ratcheted socket 220 includes a pair of diametrically opposed arcuate segments 222 from which a pair of diametrically opposed ratchet fingers 224 project forwardly from each segment, respectively. These two fingers 224 are thus circumferentially spaced from each other and are adapted to be respectively received in diametrically opposed two of the four circumferentially spaced arcuate slots 226 formed within a lost motion transmission disk 228 co-rotatable with a drive gear 230 mounted to the forward face thereof. The drive fingers 224 are adapted to transmit the rotation of the oscillatory output shaft 202 to the transmission device 228 in one direction (arrow A') only via engagement with one of the end walls 232 of two of slots 226, respectively. It is to be understood that during reverse rotation of the output shaft 202 in the direction A opposite arrow A', the fingers 224 will respectively travel through the slots 226 towards the opposite slot end wall 234. As seen from this reverse direction, the back side 236 of each finger 224 is inclined in relation to the rear axial face of the slotted transmission disk 228. Thereby, as these inclined surfaces 236 engage the opposite end wall 234 of its associated slot 226, the resulting camming contact will create a slight degree of separation which will allow each finger 224 to slide along the rear face of the transmission device 228 and then drop back into the next adjacent slot to engage the leading end wall 232 thereof. Such engagement essentially coincides with the output shaft 202 reaching the end of its oscillatory motion in the direction of arrow A so that its renewed motion in direction A' will be immediately transmitted by the fingers 224 to the transmission device 228 and thence to the uni-directional transmission gear 230.

During the aforesaid reverse oscillatory rotation of the connector 210 in the undesirable, opposite direction A, some degree of reverse rotation of the transmission disk 228 and thereby the drive gear 230 may occur as a result of frictional contact between the fingers 224 with the rear face of the transmission disk. To prevent reverse rotation of the gear 230, therefore, gear teeth 240 are formed therein to be engageable with a reverse rotation member 242 fixedly mounted to a side wall 244 of the bottom housing 208 in axial alignment with the gear teeth. The projecting end of this reverse rotation member 242 has an upwardly inclined face 246 which allows the gear teeth 240 to rotate therepast in the direction A'. However, the bottom face of member 242 is adapted to intersect the gear teeth 240 during possible reverse rotation in direction A for the prevention thereof.

A worm gear 250 is mounted for co-rotation with the drive gear 230 by means of a stub shaft 252 projecting rearwardly from the worm into press-fitting contact with a central opening 254 in the drive gear. The worm 250 is thus in coaxial alignment with the connector 210 and drive gear assembly. The uni-directional rotational movement of the worm 250 is transmitted to a speed reduction gear 256 which is mounted on a support shaft 258 projecting upwardly from the bottom wall 260 of the lower housing 208. This shaft 258 may or may not be rotatably supported on the bottom wall 260 but in either event defines a vertical axis of rotation for the speed reduction gear 256 which is perpendicular to and offset from the worm axis of rotation. This is best depicted in FIGS. 5, 6 and 7.

The speed reduction gear 256 rotates a take-up spool gear 265 which is mounted for co-rotation to a take-up spool support shaft 267 which is parallel to the speed reduction gear support shaft 258 and spaced forwardly therefrom. More specifically, the lower end of this take-up spool support shaft 267 is rotatably supported within a cylindrical mount 269 formed in the bottom wall 260 of the lower housing 208. The upper end 267 of this shaft projects upwardly through the top wall 270 of the upper housing 207 through an opening 271 to provide co-rotation for the take-up spool 204 which engages the upper end with a positive snap fit.

The diameter of the speed reduction gear 256 and the take-up spool drive gear 265 are preferably selected so that the latter rotates at approximately 10-15 rpm (preferably 12 rpm) when the flossing attachment 200 is affixed to a Braun output shaft 202 which is characterized by a high oscillatory rotational speed in either direction A, A'. This will allow the take-up spool 204 to complete one rotation every five seconds which, as a result of experimentation, has been found to be an acceptable speed for advancing the floss between successive cleaning operations of a pair of teeth.

The take-up spool 204 is functionally and structurally similar to the take-up spool 26 in the above-described manually activated embodiment. That is, the take-up spool 204 is rotated by the gear train assembly in response to an input force (in this case by mechanical activation of the motor in the electric toothbrush handle H), and this rotational movement in turn pulls the floss around the forks 34a, 34b from the supply spool 272 in a floss circuit similar to that of the manually activated embodiment 10. The take-up spool 204 is also formed with a smaller diameter portion 274 beneath a larger diameter portion 276 having an annular groove 278 designed to receive the remaining leading end of the floss after it has been initially wound onto the lower smaller diameter portion of the take-up spool several times. Unlike the manually activated embodiment 10, however, the take-up spool 204 of this embodiment 200 is prevented from reversely rotating as a result of the constant meshing engagement of the take-up spool drive gear 265 with the speed reduction gear 256, worm 250, and the drive gear 230 always engaging the reverse rotation member 242 in the lower housing 208.

Reverse rotation of the supply spool 272 is advantageously prevented by means of a simple but unique friction mechanism generally designated with reference numeral 275, which is designed to impart a sufficient spring resistance which will prevent unwinding rotational movement of the supply spool to thereby appropriately tension the floss in the circuit until the spring force is overcome by the motive force transmitted to the gear train assembly through the output shaft 202. In this embodiment, therefore, the friction mechanism 275 comprises a series of ratchet-like teeth or ridges 277 which extend radially in the top surface 270 of the upper housing 206 about a fixed and stationary mounting post 279, also projecting upwardly from the top surface of the housing at the center of the circular pattern of stationary teeth. This shaft 279 projects upwardly through a cylindrical hub 280 which is integrally formed to project upwardly from a larger diameter disk 282 also having radial teeth 284 arranged in a circular pattern in a bottom surface thereof. As best depicted in FIG. 7, these downward facing teeth 284 are adapted to engage the upward facing stationary teeth 277 when the hub 280 is mounted to the post 279. The upper teeth 284 are spring biased against the lower teeth 277 with a spring 286 received axially within the hub 280 and about the post 279. The lower end 286a of this spring 286 bears against a bottom annular wall 288 (FIG. 7) formed inside the hub 280 (the post 279 projects vertically upwardly inside the hub through a central opening 279 formed in the bottom annular wall) to press the upper teeth 284 against the lower teeth 277 under this spring bias. The length of the post 279 is slightly greater than the height of the hub 280. The post 279 thus also functions as a spring mount and a cap or washer 290 of larger diameter than the post and spring is attached to the upper end of the post to seat the upper end of the spring which is thereby compressed to a desired degree.

The hub 280 may be formed with a key 291 on an outer surface thereof which is adapted to be received in a key way 292 extending through the supply spool 272. In this manner, the supply spool 272 is co-rotationally mounted to the support hub 280 which in turn can only rotate in the unwinding direction when the spring force urging the upper teeth 284 against the lower teeth 277 is overcome by the motive force of the mechanically actuated output shaft 202.

Although not shown, it is possible to mount the spring 286 within the hub 280 of the supply spool 272 in such a manner as to variably control the spring force urging the upper and lower teeth together to thereby control the tension of the floss between the prongs 34a, 34b of the fork.

2. Rotary Attachment

FIGS. 8 and 9 are illustrations of a second embodiment 300 of a mechanically activated dental flossing device in accordance with the present invention which is adapted to be attached to the output shaft 302 of an electrical toothbrush handle 304 equipped with a motor which continuously rotates the output shaft in one rotational direction only about the shaft axis. This type of electric toothbrush handle is commercially available.

More specifically, the flossing attachment of the second embodiment 300 comprises a housing 306 which contains a worm gear 308 having a horizontal axis of rotation in coaxial alignment with the output shaft which is adapted to enter the housing through a rear open end 310 thereof upon attachment of the flossing device to the front portion of the toothbrush handle 304. Obviously, therefore, the rear end 310 of this embodiment is shaped to properly attach to the front portion of the toothbrush 310, as is the case in the other embodiments described herein. The worm gear 308 has a forwardly projecting stub shaft 312 rotatably received in a cylindrical mount 314 projecting rearwardly into the housing cavity 316 from a front end wall 318 thereof. When the flossing attachment 300 is snapped onto the cylindrically shaped forward end (not shown in detail) of the existing toothbrush handle 304, the metal output shaft 302 from the powered handle fits into a dedicated hole 320 in the worm gear 308 formed in a rear end face thereof. In this manner, the front and rear ends of the worm gear 308 are supported within the housing 306.

The worm gear 308 is therefore directly rotated about its axis while in meshing contact with a speed reduction gear 322 having a vertical axis of rotation extending perpendicular to the worm gear axis and offset therefrom as best depicted in FIG. 8. The speed reduction gear 322 is co-rotatably mounted on a support shaft 324 having a lower end 326 rotatably received in a blind bore formed in the cavity bottom wall 328, and an upper end 330 projecting upwardly from the top wall 332 of the housing 306 through a through hole formed therein. The upper end 330 of this shaft 324 is adapted to support a take-up spool 334 of identical construction to the take-up spool 204 in the first embodiment 200 of the mechanically activated device (i.e., the Braun unit) discussed supra. The take-up spool cooperates with a floss supply spool 340 of identical construction to the corresponding supply spool 272 and including the frictional mechanism 275, 277 in the aforementioned first mechanically activated embodiment 200. The floss circuit is also comprised of the prongs 34a, 34b of a fork 36 of identical construction to the first embodiment.

Therefore, the flossing operation with the second embodiment 300 is identical to that described for the first embodiment 200. The essential difference between the two embodiments 200, 300 relates to the simplified gear train in the latter as a result of receiving rotational movement from output shaft 302 which rotates in one direction only.

3. Interplak Attachment

Reference is now made to FIGS. 10–12 depicting a third embodiment 400 of a mechanically activated dental flossing device. Other than as noted specifically below, the structure and operation of the take-up spool and floss supply spool assemblies, 402, 404 as well as the remainder of the flossing circuit defined by the prongs of the fork are identical in construction and operation to the corresponding assemblies in the first and second embodiments 100, 200. It is to be noted, however, that in the third embodiment 400, the positions of the assemblies 402, 404 are reversed in relation to the other embodiments.

The dental floss attachment 400 of this embodiment is adapted to be mounted to a mechanical output shaft 406 of an electric toothbrush handle 408 (FIG. 11 only) containing a motor which reciprocates its shaft in back and forth strokes A, A' along the longitudinal shaft axis. This type of motion is characteristic of a commercially available electric toothbrush handle sold by Interplak, manufactured by Bausch & Lomb, Tucker, Ga.

The flossing attachment 400 according to this third embodiment is comprised of a top housing 410 and a bottom housing 412 which may be screwed or pinned together to define an internal cavity 414 adapted to contain the unique gear train assembly of this embodiment. Each of the top and bottom housings 410,412 are formed with elongated rearwardly extending portions 416 (extending to the left in the drawing figures) which define an elongate cavity 418 adapted to receive the shaft 406 and which contains a horizontally extending rack 420 formed with gear teeth 422 in one vertical side thereof. The rearward or left-handmost opening of these housings 416 defines an entrance socket 424 which is adapted to mate with a front end portion (not shown) of the electric toothbrush handle 408. The output shaft 406 of the handle 408 projects forwardly through the socket 424 into the elongate cavity 418 for connection to the rear end of the rack 420. For that purpose, a plurality of rearwardly and outwardly projecting flexible fingers 426 extend from the rear end to encompass the front end of the shaft 406. These fingers 426 are then clamped to the front end by means of a slidable locking sleeve 428 which is indexed rearwardly to encircle the fingers and press them into firm radially inward clamping contact with the shaft.

The rack gear 420 slides back and forth in the housing 412 in reciprocating strokes A, A' as the output shaft 406 of the electric toothbrush handle 408 is plunged backward and forward by the existing power unit in the handle via the clipped engagement 426, 428 with the rack gear. A stop 421 prevents withdrawal of the rack 420 through the socket. The rack teeth 422 in turn engage a small pinion gear 430 which is mounted to the lower end of a vertical support shaft 432 rotatably received in a cylindrical blind bore 434 formed in the lower cavity wall 436 of the bottom housing 412. This shaft 432 is rotatable about its axis relative to the bottom mounting for purposes described hereinafter. The small diameter pinion gear 430 is loosely mounted on this shaft 432 so as to be relatively independently rotatable thereon about the vertical shaft axis. In this manner, the small pinion gear 430 is in constant meshing engagement with a larger diameter gear 438 which is mounted on a stationary support shaft or post 440 having a bottom end received in another cylindrical blind bore formed in the lower wall 436 of the bottom housing cavity. The upper end 442 of this support shaft is received in a downwardly facing blind bore 444 formed in the lower surface of the top wall 446 of the upper housing 410. This post 440 thus defines a vertical axis of rotation for the gears mounted thereon.

The large diameter gear 438 mounted to this post 440 in meshing contact with the pinion gear 430 is thus caused to rotate about its mounting shaft axis in a back and forth oscillatory motion as a result of its driven contact with the pinion which is in turn rotated back and forth by the reciprocating rack gear 420. To convert this oscillatory gear motion into uni-directional rotary motion, a pair of diametrically opposed ratchet fingers 450 project upwardly from a ratchet member 452 mounted on the upper surface of the large diameter gear 438 for reception respectively in one of a series of driving slots 454 formed at circumferentially spaced intervals in a second large diameter gear 456 also coaxially mounted on the second support post 440.

The ratchet fingers 452 engageable with the lost motion slots 454 formed in the gear 456 function in the same manner as the ratchet and lost motion transmission arrangement 224, 228 disclosed in the first embodiment 200 so that rotation of the oscillating gear 438 in one direction only is transmitted by the ratchet fingers 452 into the upper large diameter gear 456 via driving contact with the lost motion slots 454 while the undesirable rotation of the oscillating gear in the reverse rotational direction is used to index the ratchet fingers through the slots and into the next adjacent circumferential slots for renewed driving direction when reverse rotation ends.

The large diameter second gear 456 thus essentially performs the same function as the lost motion transmission disk 228 and drive gear 230 of the first embodiment 200, and has gear teeth 460 whose sole function is to engage a second ratchet projection 462 mounted in the lower cavity wall 436 of the bottom housing 412 to prevent reverse rotation of the rotary drive gear 456. As in the first embodiment, this reverse rotational movement is likely to occur as a result of frictional contact between the ratchet fingers 450 with the underside of the rotary gear 456 during reverse rotation of the coaxially mounted oscillatory gear 438 in the lost motion direction of the fingers.

A small diameter gear 464 is coaxially mounted on the second post 440 above the rotary gear 456 (and may be integral therewith) for co-rotation in order to transmit uni-directional rotational movement to a larger diameter take-up spool drive gear 466 which may be mounted on the first support shaft 432 immediately adjacent the lower surface of the top housing wall 446 as best depicted in FIG. 12. This take-up spool drive gear 466 is adapted to rotate its support shaft 432 without rotating the pinion 430 which is loosely mounted on a lower portion of this shaft for independent oscillatory driving movement by the rack gear 420. In this manner, uni-directional rotation is transmitted by this large diameter gear 466 to the take-up spool assembly 402 which is mounted to a portion of the support shaft projecting upwardly through the top wall 446 of the upper housing 410. In the alternative, the take-up spool drive gear 466 and the take-up spool 402 may be mounted on a separate stub shaft (not shown) so as not to be dependent on the location of the support shaft 432 in the bottom housing 412.

The take-up spool 402 may have the same construction as the spool in the first and second embodiments 200, 300 as mentioned above. Floss supply spool assembly 404 is also mounted to the outer surface of the upper housing 410 and is forwardly offset from the take-up spool 402. This supply spool assembly 404 is also identical in construction and operation to the supply spool assembly in the first and second embodiments.

It will be apparent that various combinations of the elements of each embodiment can be made to produce an effective flossing device. It will also be evident that various packaging techniques can be utilized to make the device more attractive, including that of scaling down the device to a child's size. These and other variations are considered to be within the scope of the invention.

The important features of the present invention with respect to each of the manual and mechanical embodiments primarily relate to the advantageous placement of the take-up spool outside of the housing while confining the gear train assembly therein to avoid an unhygienic situation, while allowing for easy threading or re-threading of the floss to establish the floss circuit. This is important when considering that the floss will typically break at least one during a daily flossing regimen as a result of abrasion or breaking due to contact with tight spaces. To encourage use of the flossing devices of these inventions, it is therefore imperative that the user be easily able to re-establish the floss circuit with minimal hassle.

It is equally important that an appropriate degree of tension be imparted to the floss stretched across the space between the prongs of the flossing fork. This is achieved in the different embodiments of the present invention in the specific manner described in detail above, but generally by utilizing the locked gear train to prevent reverse rotation of one of the spools while utilizing a simple yet effective ratchet mechanism (manual flosser), or strong frictional resistance created by the spring biased tooth arrangements, for preventing reverse rotation of the spool in the different embodiments.

Figure 16:
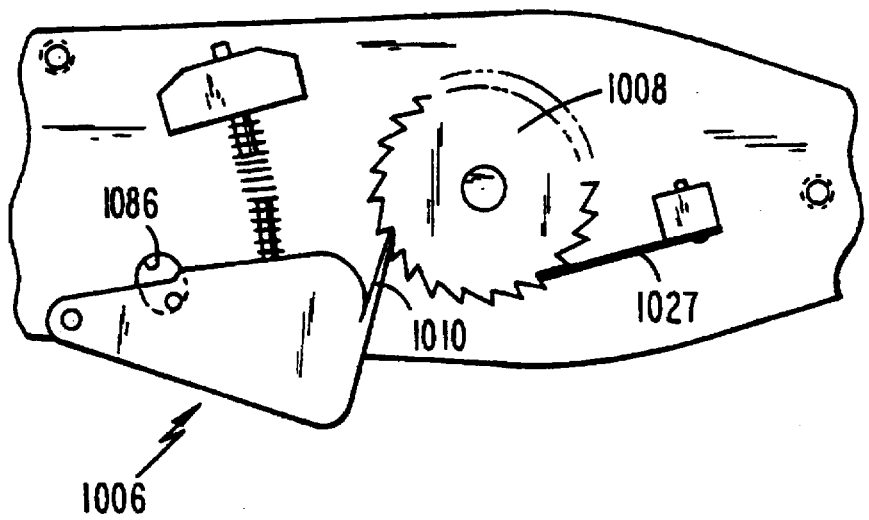
FIG. 16 is an enlarged, partial plan view of a take-up spool ratchet assembly in the hand-held flosser of FIG. 13.

FIG. 13 is an exploded perspective view of a preferred embodiment of a manual dental flossing device 1000 comprised of a handle formed from a top housing 1002 and a bottom housing or closure plate 1004 containing a uniquely arranged spring-loaded trigger mechanism, generally designated by reference numeral 1006, protruding laterally from between the housings. Manually depressing the trigger mechanism 1006 is operable to partially rotate a take-up spool drive wheel 1008 in one direction A only through advancement of a driving pawl 1010, attached to the trigger, into contact with ratchet teeth 1012 (FIG. 15) formed on the take-up spool drive wheel 1008. Wheel rotation winds preferably used floss 1014 onto a take-up spool 1016, co-rotatably mounted on the same shaft axis 1018 as the take-up wheel 1008, and located advantageously above the top housing 1002. As this winding action occurs during depressing of trigger 1006 (FIG. 17), a floss supply spool 1020, advantageously located in an interior compartment 1022 disposed in the back end of the top housing 1002, is simultaneously rotated in an unwinding direction B as a result of overriding a slip clutch for similar ratchet mechanism 1025 as discussed more fully below. This allows fresh floss 1112 to be progressively advanced in a flossing circuit where it is stretched and tensioned across a space 32 formed between a pair of identical prongs 34 of a fork 36 which defines a forwardly extending portion of the top housing 1002 in the same manner as the forked extension in the manual dental flossing device 10 discussed, supra. Release of the trigger mechanism 1006 causes the driving pawl 1010 and the trigger to return back to the 'home' or undepressed trigger position (FIG. 16). A ratchet finger or stop pawl 1027 advantageously prevents reverse rotation of the floss take-up spool drive wheel 1008 so that the floss supply circuit remains highly tensioned to avoid slack in the floss in space 32.

Referring to FIGS. 13 and 14, it can be seen that the top housing 1002 is in the form of an elongated substantially flat cover plate extending rearwardly from the curved fork 36. Unlike top housing 12 in the flossing device 10 described above, however, the top housing 1002 in the preferred embodiment features a covered cylindrical rear housing 1030 with interior cavity 1022 adapted to contain floss supply spool 1020. The floss supply spool housing cavity 1022 is defined by a circular bottom wall 1032 and a cylindrical side wall 1034 having a diameter which is greater than the diameter of a full floss supply spool (FIGS. 13 and 14). Side wall 134 terminates in an upward facing circular opening which is selectively covered (FIG. 15) or uncovered (FIG. 14) by means of a circular cover plate 1036 pivotally secured to the top housing 1002 with a pivot pin 1038. A stop ridge 1040 subtending a predetermined angular interval of less than 180° is formed partly around the circular opening to act as an abutment when the cover plate is pivoted into the closed position (FIG. 15). A groove 1042 (FIG. 14) formed in the stop ridge 1040 allows the passage of floss from the supply spool 1020 along the top surface 1002a of the housing 1002 to establish the floss circuit around fork extension 36. A rounded protuberance 1044 projecting downward from the lower surface of cover 1036 acts as a locking detent to maintain the cover in closed position.

In this preferred embodiment, the floss take-up spool 1016 constitutes the sole structure in the floss supply circuit which is located outside the housings 1002,1004 to advantageously avoid contamination within the housings by used floss and to enable easy cleaning with water to prevent the occurrence of an unhygienic situation. In this preferred embodiment, it is desirable to locate the floss supply spool 1020 within interior housing compartment 1022 in order to (1) minimize contamination and (2) allow the user to securely hold the flossing device 1000 by gripping the rear portion of the housing 1002 and the floss supply spool housing 1030 in particular as a handle without encountering the floss supply spool as an obstruction which might otherwise occur in the embodiment of FIG. 1.

FIG. 15 is a bottom plan view of flossing device 1000 with the bottom housing or cover 1004 removed to enable viewing of the trigger mechanism 1006 and take-up spool drive wheel 1008 located within the compartment formed between the top and bottom housings. Solid lines 1046,1046' depict the forwardmost and rearwardmost extent of the bottom cover plate 1004. As best depicted in the perspective view of FIG. 13, bottom cover 1004 is formed with a bottom wall 1050 with upwardly projecting sides 1052 and a cutout 1054 formed in one of the sides through which the trigger 1006 extends into the FIG. 15 undepressed condition. Bottom cover 1004 may be secured to top cover 1002 with screws 1055.

The take-up spool supply wheel 1008 is located within an interior compartment defined by the parallel interior faces 1002b,1050a of the top and bottom walls formed in the associated housings and is rotationally supported through upper and lower shaft projections 1056 and 1058 respectively received within aligned through holes 1060 and 1062 formed in the top and bottom walls. The lower shaft projection 1058 terminates within the lower throughbore 1062 while the upper shaft projection 1056 extends outwardly from the top wall 1002a into press-fitting non-rotational engagement with a downwardly projecting shaft stub 1064 in the take-up spool 1016. In this manner, rotation of the take-up spool drive wheel 1008 is transmitted to the take-up spool 1016 as discussed infra.

The trigger mechanism 1006 is used to incrementally rotate the take-up spool drive wheel 1008 by advancing driving pawl 1010 into meshing contact with one of ratchet teeth 1012 upon depressing the trigger. As best depicted in FIG. 15, the trigger 1006 is a triangular or sector shaped member, preferably of uniform thickness, having a rearwardly projecting apex 1066 pivotally secured within the compartment via upper and lower pin projections 1068 received in aligned throughbores 1070 respectively formed in the top and bottom walls 1002a,1050. The trigger includes a manually depressible portion 1072 protruding outwardly through the cutout 1054 into its outwardmost neutral position (FIG. 15) under the action of a compression spring 1074 having opposite ends in respective abutment with the trigger and a fixed spring rest 1076 attached to the interior face 1002b of the top housing wall 1002a. More specifically, the fixed spring rest 1076 and the opposing surface defining the interior triangular side 1078 of the trigger 1006 respectively support a pair of projections 1080 respectively received within the spring ends to maintain the spring 1074 in its proper position. The outwardmost extent of the trigger 1072 is defined via contact between a pin 1084 projecting downwardly from the trigger (intermediate the pivot pin 1068 and spring rest 1080) engaging the outer end of an elongate slot 1086 formed in the interior surface 1002b of the top wall 1002a.

Figure 17:
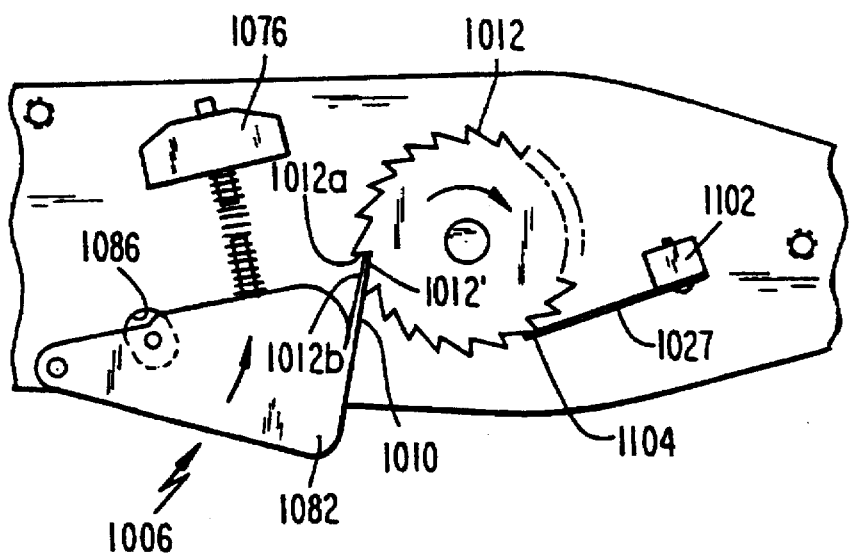
FIG. 17 is a view similar to FIG. 16 depicting the relative positions of the driving stop pawls in the ratchet assembly of the hand-held flosser of FIG. 13 during trigger depressing.

As the trigger 1006 is depressed inwardly into the compartment against the bias of spring 1074, driving pawl 1010 enters into meshing contact with one of the ratchet teeth 1012 of take-up spool drive wheel 1008 to rotate same through a predetermined arcuate interval. As best depicted in FIG. 17, the pawl 1010 may be integrally formed with the forward distal portion 1082 of the trigger 1006 to have a distal end 1010a adapted to contact the gear teeth 1012. As the trigger 1006 is depressed, distal end 1010a is advanced into pushing contact with a generally radially extending wall 1012a of a tooth 1012 to rotate wheel 1008 about its axis of rotation 1018 (FIG. 17).

Although driving pawl 1010 is disclosed as being integral with trigger 1006, other materials and configurations can be used in substitution therefor. For example, the pawl 1010 may be made as a separate member. In addition, pawl 1010 may be substituted with a rack attached to trigger 1006 and having a series of rack teeth adapted to mesh with teeth formed in a take-up spool drive gear or with the ratchet teeth of wheel 1008.

Trigger release allows the compressed spring 1074 to bias the trigger 1006 back to its home position depicted in FIGS. 15 and 16. As the trigger 1006 pivots back (FIG. 16) to its home position, the distal end 1010a of the driving pawl 1010 travels out of driving engagement with one of ratchet teeth 1012 where it will ride over the generally circumferentially extending inclined wall 1012b of the trailing ratchet tooth 1012. In the preferred embodiment, undesirable reverse rotation of the take-up spool drive ratchet 1008 during trigger release is advantageously prevented by means of stop pawl 1027 functioning as a one-way clutch mechanism. As best depicted in FIG. 17, this stop pawl 1027 has one end secured to a stationary support projection 1102 formed in the forward portion of the top wall interior face 1002b. This pawl 1027 projects rearwardly and has a rear distal end 1104 which will positively engage with the take-up spool drive teeth 1012 during trigger release. In other words, this distal end 1104 engages a wall 1012a to prevent reverse rotation of the ratchet 1008 as the distal end 1010a of the driving pawl rides up and over the teeth during trigger release. However, during trigger depressing (FIG. 17), the distal end 1104 of the stop pawl 1027 is configured to ride up and over the ratchet tooth wall 1012b as the ratchet is advanced by the driving pawl 1010 in the winding direction of the take-up spool 1016.

The stop pawl 1027 as used in the preferred embodiment defines a very simple but reliable one-way clutch mechanism to prevent reverse rotation of the take-up spool drive wheel 1008.

The feature of a ratchet mechanism comprised of a driving pawl 1010 and stop pawl 1027 in the preferred embodiment avoids the need for multiple gears as employed in the FIG. 1 embodiment of dental flossing device 10. This in turn allows a large diameter take-up wheel 1008 to be used which, in combination with appropriate sizing and placement of trigger 1006 and driving pawl 1010, will result in sufficient mechanical advantage to enable individuals with weak hand grips to exert enough pressure to depress trigger 1006 without compromising floss tension.

In the presently preferred embodiment, floss supply spool 1020 is advantageously located within interior compartment 1022 disposed in the rearwardmost portion of the top housing 1002. This interior placement advantageously isolates the fresh spool from possible contamination with spent floss accumulating on the take-up spool 1016 and also prevents undesirable contact with the user's hand during gripping and manipulation of the dental flossing device 1000, as tended to occur with the dental flossing device 10 discussed, supra. In other words, by placing the supply spool 1020 within the interior compartment 1022, the user can now place the palm portion of their hand, or the base of their forefinger, on the upper surface of closed cover plate 1036 while allowing their thumb and forefinger to rest against the opposing side surfaces of the top and bottom housings 1002,1004, with the trigger 1006 being depressed by the forefinger, all without contacting the floss on the supply spool or within the circuit.

With reference to FIG. 13, the floss supply spool 1020 is preferably in the form of a cylindrical spool 1110 (e.g., plastic) on which fresh floss 1112 is wound. The supply spool 1020 is easily mounted by the user on supply spool support shaft arrangement 1025 projecting upwardly in the storage compartment 1022 from the bottom wall 1032 thereof. As best depicted in FIG. 13A, this support shaft arrangement 1025 is formed with a key 1115 adapted to interfit with a vertical key guide 1117 formed on the inner cylindrical surface of the supply spool 1110. As a result of this keyed connection, the floss supply spool is easily detached from the support shaft to advantageously allow for easy and rapid replacement of an empty floss supply spool with a fresh spool. It will therefore now be understood that the present invention allows for use of pre-wound replacement spools of floss which are specially made so that the supply spools 1110 are keyed or otherwise adapted to easily interfit onto the supporting shaft arrangement 1025 for easy removal and placement thereon. The floss on each of these pre-wound spools is preferably evenly machine wrapped onto the supply spool 1110 with the floss leader initially contacting the supply spool preferably tied or otherwise fixed to the spool so as to maintain tension in the floss circuit as the supply spool approaches empty. These pre-wound supply spools may be sold together with the flosser of FIG. 13 in a kit form, or may be available for individual purchase to replenish the floss supply.

The support shaft arrangement 1025 is formed with a lower support shaft portion 1120 fixed to the storage compartment bottom wall 1032 and an upper shaft portion 1122 formed with the keyed connection 1115 and mounted to the lower shaft portion. The upper surface of the lower shaft portion 1120 is formed with a series of triangular shaped teeth 1124 meshing with an array of like bottom teeth 1126 formed in a cylindrical bottom recess 1127 of the upper shaft cylindrical portion 1122. The lower shaft portion 1120 projects into recess 1127 for improved centering and support. These teeth 1124,1126 are urged into contact with each other by means of a tension spring 1128 located within an upper cylindrical recess 1130 formed in the upper shaft portion 1122. The lower end of the compression spring 1128 is seated against the recessed bottom wall 1132 formed in recess 1130. The upper end of the spring is captivated against the lower surface of a screw head 1134 of a tension adjustment screw 1136. The screw shank 1138 extends through both the tension spring 1128 and a through bore 1137 located between recesses 1127,1130, with the lower end 1139 in threaded engagement with a threaded bore 1140 in lower fixed shaft 1120. This configuration and equivalent tensioning arrangements which will now occur to one of ordinary skill, enables transmission of spring force to urge teeth 1126 in the upper shaft portion 1122 against the teeth 1124 in the lower shaft portion. In this manner, the teeth formed in the upper and lower shaft portions act as a slip clutch which enables floss 1112 to be stripped from the spool 1020 during trigger depressing (i.e., the upper teeth ride up and over the lower teeth against bias of spring 1128 during rotation of upper shaft portion 1122 on which the floss spool is mounted) while maintaining appropriate tension through the supply spool on the supply end of the floss circuit.

It will be appreciated that screw 1136 may be rotated to adjust the tension of spring 1128 which in turn directly affects the tension in the floss circuit. Screw 1136 may be turned with a screwdriver. In the alternative, it will now be appreciated by one of ordinary skill that screw head 1134 may be suitably provided with a knurled or other type of manual gripping profile to facilitate tension adjustment.

FIGS. 13C–13F constitute an alternate embodiment to the spring and screw adjustment mechanism depicted in FIG. 13B. Therein, fixed lower shaft portion 1120 is replaced with a fixed ratchet wheel 1200 integrally formed to project upward from bottom wall 1032. Ratchet wheel 1200 is formed with vertically extending ratchet teeth 1202 as best depicted in FIGS. 13C and 13F. A clutch member 1204 formed with a pair of diametrically opposed curved fingers 1206 respectively provided with a ratchet pawl 1208 at opposite distal ends thereof (FIG. 1E) is mounted for rotation on ratchet wheel 1200. A cylindrical sleeve 1210 formed with a large diameter bottom recess 1212 extending through a major portion thereof receives the clutch therein in press-fitting engagement. A pin 1214 having a lower end press-fitted into an axial blind bore 1216 formed in ratchet wheel 1200 is used to secure the clutch components together. The arrangement of ratchet teeth 1202 and pawls 1208 in engagement therewith functions as an alternative means for tensioning the supply spool and the floss circuit.

In operation, floss supply spool 1020 is easily loaded into flossing device 1000 in the preferred embodiment by first pivoting cover 1036 into the open position of FIG. 13. Supply spool 1020 is then loaded by inserting the upper end of upper shaft portion 1122 into the lower end of cylindrical spool 1110 as the spool is lowered onto the support shaft arrangement 1025 with key 1115 in proper alignment with key guide 1117. When the spool is properly seated within compartment 1022, the user then grips the free end of the floss and exerts pressure to strip a length of floss from the spool against the bias of the slip clutch mechanism discussed above.

The strip floss leader is then fed into the guide groove 1042 by simply lowering it into the open groove. At this point, cover 1036 may now be pivoted into its closed position (FIG. 15). The floss leader is then positioned around the fork 36 and the leading end of the floss is then wrapped several times around take-up spool 1016 before being secured into notch 1150 thereon. The flossing device 1000 is now ready for use.

FIGS. 18 and 19 are illustrations of a variation within flossing device 1000 wherein trigger mechanism 1006 is eliminated and replaced with a knob fixedly mounted on take-up spool 1016 which is manually rotatable in direction A to advance floss in the supply circuit with rotation of ratchet wheel 1008 through rotation of shaft portions 1056, 1064 or equivalents thereof. The manually rotatable knob, generally designated with reference numeral 1400 is preferably formed with circumferentially spaced finger-gripping depressions 1402 in a top surface thereof. This alternate embodiment results in the elimination of trigger mechanism 1006 and driving pawl 1010 although stop pawl 1027 is still utilized to prevent reverse rotation of ratchet wheel 1008.

Figure 20:
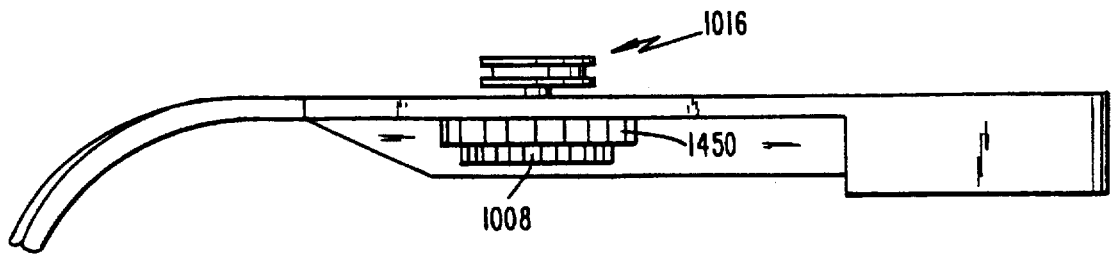
FIG. 20 is a side plan view of another embodiment of the hand-held flosser of FIG. 13.
Figure 21:
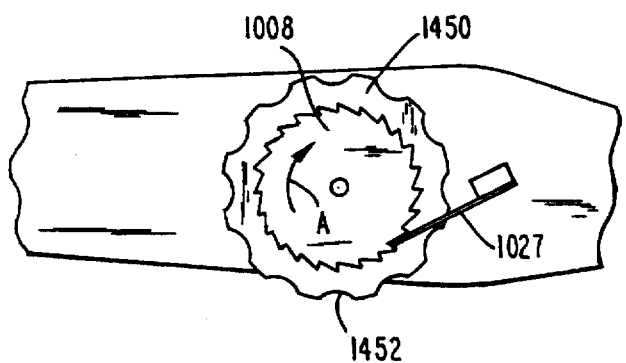
FIG. 21 is a plan view of the housing interior in the embodiment of FIG. 20.

FIGS. 20 and 21 are illustrations of another variation within flossing device 1000 wherein trigger mechanism 1006 is eliminated and replaced with a finger wheel 1450 which is fixedly mounted on take-up spool shaft portion 1056 for co-rotation with ratchet wheel 1008. With reference to FIG. 21, a peripheral portion of finger wheel 1450 projects outwardly from the housing interior for finger-gripping actuation and thereby manual rotation by the user in direction A to advance floss in the supply circuit with rotation of ratchet wheel 1008 through rotation of shaft portions 1056, 1064 or equivalents thereof to maintain tension at the take-up end. The manually rotatable finger wheel 1450 is preferably formed with circumferentially spaced finger-gripping depressions 1452 along the periphery thereof. This alternate embodiment, as in the case of the FIGS. 18 and 19 embodiment, also results in the elimination of trigger mechanism 1006 and driving pawl 1010 although stop pawl 1027 is still utilized to prevent reverse rotation of ratchet wheel 1008.

In each of the foregoing, hand-held manual flosser embodiments of FIGS. 13–20, it will now be appreciated that other variations are possible without departing from the scope of the present invention. For example, although the preferred embodiments utilize a ratchet mechanism connected to the supply spool to cooperate with the ratchet mechanism 1008 to tension the floss, other tensioning mechanisms are possible. For example, the so-called ratchet mechanism afforded by teeth 1124,1126 may be replaced by elimination of these teeth in favor of another type of slip clutch mechanism or, for example, a drag type of mechanism (adjustable or non-adjustable) as commonly used in spin fishing reels and bait casting reels for controlling the drag or tension of fishing line. Therefore, these teeth may be replaced, for example, with one or more synthetic or metal washers imparting friction to resist unwinding rotation of supply spool 1020.

It is theorized that the so-called ratchet mechanism afforded with teeth 1124,1126 may also be replaced with other types of tensioning mechanisms, such as the elimination of the aforesaid teeth with the placement of a pin spaced away from the supply spool and extending generally parallel to the axis of rotation of the supply spool. It is believed that a couple of turns of floss around this pin may be sufficient to appropriately tension the floss in the circuit at the supply end thereof.

It will also be appreciated that forked extension 32, as the term is used herein, is also intended to cover the use of other projections extending from the housing which define a space between the projections between which floss may extend.

Figure 22:
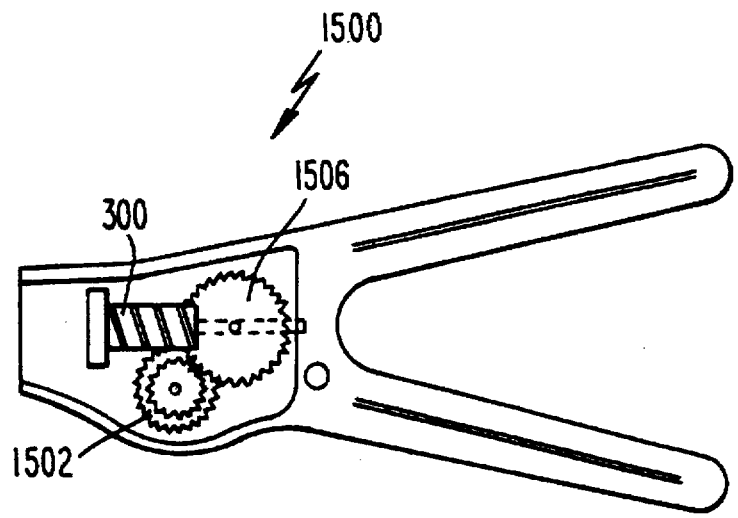
FIG. 22 is a top plan view of an alternative embodiment to the second embodiment of a mechanically actuated flossing attachment depicted in FIG. 8.
Figure 23:
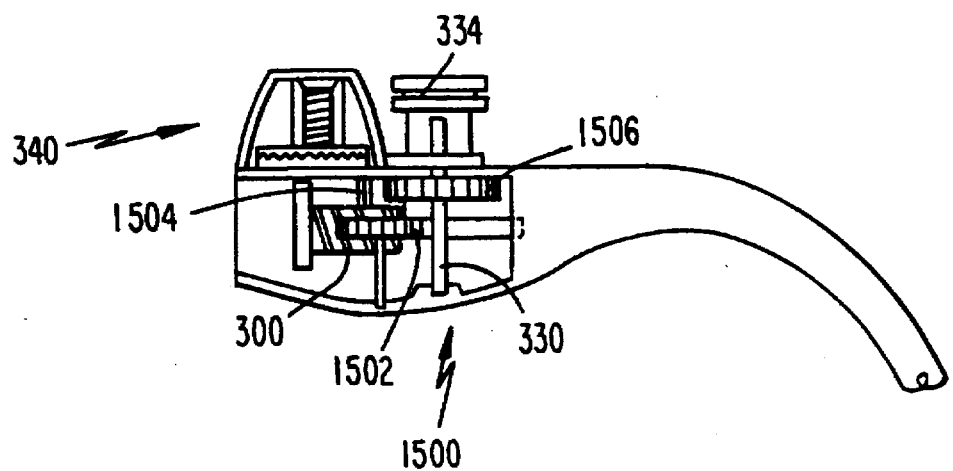
FIG. 23 is a side elevational view of the FIG. 20 embodiment.

FIGS. 22 and 23 are illustrations of a variation to the second embodiment 300 depicted in FIGS. 8 and 9. This variation in FIG. 22 and 23 is generally designed with reference numeral 1500. The sole distinctions between embodiments 300 and 1500, which for the most part utilize the same reference numerals, reside in the use of a speed reduction gear train in the embodiment 1500 wherein worm 300 is utilized to drive a first speed reduction gear 1502 which changes the orientation of rotation from a horizontal to a vertical axis. Gear 1502 rotates smaller diameter gear 1504 which is coaxially mounted above gear 1502 for co-rotation therewith on a vertical support shaft having opposite ends rotatably secured in the top and bottom housing walls. This smaller diameter gear 1504 in turn rotates a larger diameter take-up spool drive gear 1506 which serves as a further speed reduction gear.

Therefore, flossing operation with the alternate embodiment 1500 is identical to that described for the second embodiment 300. The essential difference between the two embodiments 300,1500 relates to the further speed reduction obtained with the speed reduction gear train in the latter embodiment which will result in a slower take-up rotational speed in the second embodiment relative to the second embodiment 300.

It will be readily seen by one of ordinary skill in the art that the present invention fulfills all of the objects set forth above. After reading the foregoing specification, one of ordinary skill will be able to effect various changes, substitutions of equivalents and various other aspects of the invention as broadly disclosed herein. It is therefore intended that the protection granted hereon be limited only by the definition contained in the appended claims and equivalents thereof.

It will be evident that there are additional embodiments which are not illustrated above but which are clearly within the scope and spirit of the present invention. For example, it is within the scope of this invention to mount a floss cutter in the form of a metal tongue (not shown) to the housing of any of the above and additional embodiments to cut any extraneous ends or undesirable floss lengths from the floss circuit. The above description and drawings are therefor intended to be exemplary only in nature and the scope of the invention is to be limited solely by the appended claims.

We claim:

1. A flossing device to facilitate the insertion of floss between teeth, comprising:
    a) a housing including a forked extension extending from said housing and having a pair of prongs with grooves for guiding said floss in a circuit which spans a space between said prongs;
    b) a floss supply spool rotatably mounted to said housing;
    c) a floss take-up spool rotatably mounted to said housing outside thereof;
    d) an actuating mechanism for rotating said take-up spool to advance floss within the floss circuit;
    e) a first ratchet mechanism connected to the floss take-up spool to tension the floss during periods when the actuating mechanism is de-activated; and
    f) a second ratchet mechanism connected to the supply spool to cooperate with the first ratchet mechanism to tension the floss during periods when the actuating mechanism is de-activated.

2. The flossing device of claim 1, wherein said first ratchet mechanism is rotatable to rotate the take-up spool in a winding direction when rotated by operation of said actuating mechanism.

3. The flossing device of claim 2, wherein said actuating mechanism is a trigger projecting from the housing and including a driving pawl engageable with the first ratchet mechanism during actuation of said trigger.

4. The flossing device of claim 3, wherein said first ratchet mechanism includes a ratchet wheel and a stop pawl adapted to lock up and prevent reverse rotation of the ratchet wheel during de-actuation of said trigger.

5. The flossing device of claim 1, wherein said supply spool is located in a separate compartment within the housing.

6. The flossing device of claim 5, further comprising a cover which is movable to selectively cover and uncover the compartment interior in which the supply spool is located.

7. The flossing device of claim 1, wherein said take-up spool is located outside said housing.

8. The flossing device of claim 1, wherein said actuating mechanism is a knob located outside said housing.

9. A flossing device to facilitate the insertion of floss between teeth, comprising:
    a) a housing including a forked extension extending from said housing and having a pair of prongs with grooves for guiding said floss in a circuit which spans a space between said prongs;
    b) a floss supply spool rotatably mounted to said housing;
    c) a floss take-up spool rotatably mounted to said housing;
    d) a depressible trigger including an actuating member;
    e) a first mechanism connected to the floss take-up spool to tension the floss during periods when the actuating member is de-activated, said first mechanism being contacted by said actuating member to advance said floss in said circuit; and
    f) a second mechanism connected to said supply spool and cooperating with the first mechanism to tension the floss.

10. The flossing device of claim 9, wherein said take-up spool is located outside said housing.

11. A method of flossing, comprising:
    a) depressing a trigger of a flossing device to automatically advance floss in a flossing circuit of the device by an incremental amount without further manual manipulation of the floss;
    b) releasing said trigger;
    c) flossing with said trigger released by inserting a portion of said device into the user's mouth, said portion including exposed floss in a tensioned circuit; and
    d) repeating steps a) through c);
    wherein step c) occurs with said trigger released throughout the entire flossing operation regardless of space between the teeth.

12. A flossing device to facilitate the insertion of floss between teeth, comprising:
    a) a housing including a forked extension extending from said housing and having a pair of prongs with grooves for guiding said floss in a circuit which spans a space between said prongs;
    b) a floss supply spool rotatably mounted to said housing;
    c) a floss take-up spool rotatably mounted to said housing outside thereof;
    d) an actuating mechanism for rotating said take-up spool to advance floss within the floss circuit;
    e) a first mechanism connected to the floss take-up spool to tension the floss during periods when the actuating mechanism is de-activated, said first mechanism being contacted by said actuating mechanism to advance said floss in said circuit; and
    f) a second mechanism connected to and operable only on said supply spool and cooperating with the first mechanism to tension the floss during periods when the actuating mechanism is de-activated;
    wherein said first and second mechanisms operate to maintain tension in the floss circuit without manual intervention.

13. A flossing device to facilitate the insertion of floss between teeth, comprising:
    a) a housing including a forked extension extending from said housing and having a pair of prongs with grooves for guiding said floss in a circuit which spans a space between said prongs;

b) a floss supply spool rotatably mounted to said housing;

c) a floss take-up spool rotatably mounted to said housing thereof;

d) an actuating mechanism for rotating said take-up spool to advance floss within the floss circuit;

e) a first mechanism connected to the floss take-up spool to tension the floss during periods when the actuating mechanism is de-activated, said first mechanism being contacted by said actuating mechanism to advance said floss in said circuit; and f) a second mechanism connected to and operable only on said supply spool and cooperating with the first mechanism to tension the floss during periods when the actuating mechanism is de-activated;

wherein said take-up and supply spools respectively have axes of rotation which are parallel to each other and substantially perpendicular to the floss in the floss circuit.

14. A flossing device to facilitate the insertion of floss between teeth, comprising:

a housing including a forked extension extending from said housing and having a pair of prongs with grooves for guiding said floss in a circuit which spans a space between said prongs;

a floss supply spool rotatably mounted to said housing;

a floss take-up spool rotatably mounted to said housing and outside thereof;

a gear train assembly within said housing for rotating said take-up spool in a winding direction to receive used floss from said space;

a actuating mechanism for actuating said gear train assembly to rotate said take-up spool;

wherein said gear train assembly is arranged to lock up and prevent reverse rotation of at least one of the take-up spool or supply spool;

a ratchet mechanism connected to at least one of the other of said take-up or supply spools to cooperate with the locked gear train assembly to tension the floss during periods when the actuating mechanism is deactivated, wherein the flossing device is in the form of an attachment to a hand-held motorized toothbrush handle equipped with a motor from which projects an output shaft, which functions as said actuating mechanism, said housing being formed with a rear open end to receive a forward end of the toothbrush handle in connecting engagement with said output shaft thereby extending into the housing; and means in said housing for connecting said output shaft to the gear train assembly, wherein said gear train assembly further includes a first speed reduction gear assembly meshing with a worm mounted for co-rotation with the output shaft and a take-up spool drive gear meshing with the first speed reduction gear assembly, said drive gear being mounted on a support shaft projecting through the housing to the exterior thereof to support the floss take-up spool co-rotatably mounted thereon, wherein said take-up spool is locked against rotation by the gear train assembly during non-rotation of said output shaft.

15. A flossing device to facilitate the insertion of floss between teeth, comprising:

a housing including a forked extension extending from said housing and having a pair of prongs with grooves for guiding said floss in a circuit which spans a space between said prongs;

a floss supply spool rotatably mounted to said housing;

a floss take-up spool rotatably mounted to said housing and outside thereof;

at least one gear within said housing for rotating said take-up spool in a winding direction to receive used floss from said space;

an actuating mechanism for actuating said at least one gear to rotate said take-up spool;

wherein said at least one gear is arranged to lock up and prevent reverse rotation of at least one of the take-up spool or supply spool;

a ratchet mechanism connected to at least one of the other of said take-up or supply spools to cooperate with the locked at least one gear to tension the floss during periods when the actuating mechanism is deactivated.

16. A flossing device, comprising a floss circuit including a take-up spool and a supply spool between which floss extends; an actuating mechanism, including a trigger having a depressible trigger portion projecting from an interior of said device, for rotating the take-up spool to wind used floss thereon and simultaneously advance fresh floss into a flossing location of the circuit; means for locking and preventing reverse rotation of at least one of the take-up and supply spools; and a mechanism connected only to the other of said take-up or supply spools to cooperate with the locking means to tension the floss during periods of deactivation of the actuating mechanism.

17. A flossing device to facilitate the insertion of floss between teeth, comprising:

a housing including a forked extension extending from said housing and having a pair of prongs with grooves for guiding said floss in a circuit which spans a space between said prongs;

a floss supply spool rotatably mounted to said housing;

a floss take-up spool rotatably mounted to said housing and outside thereof;

a gear train assembly within said housing for rotating said take-up spool in a winding direction to receive used floss from said space;

an actuating mechanism for actuating said gear train assembly to rotate said take-up spool;

wherein said gear train assembly is arranged to lock up and prevent reverse rotation of at least one of the take-up spool or supply spool;

a ratchet mechanism connected to at least one of the other of said take-up or supply spools to cooperate with the locked gear train assembly to tension the floss during periods when the actuating mechanism is deactivated.

18. The flossing device of claim 17, wherein the floss circuit is located exclusively outside the housing.

19. The flossing device of claim 17, wherein the flossing device is in the form of an attachment to a hand-held motorized toothbrush handle equipped with a motor from which projects an output shaft, which functions as said actuating mechanism, said housing being formed with a rear open end to receive a forward end of the toothbrush handle in connecting engagement with said output shaft thereby extending into the housing; and means in said housing for connecting said output shaft to the gear train assembly.

20. The flossing device of claim 19, wherein said output shaft oscillates in opposite rotational directions through predetermined arcuate intervals, said connecting means including:

a connector engageable at one end thereof with the output shaft, the other end of said connector including at least a pair of axially extending fingers projecting forward from the connector;

a lost motion transmission disk containing plural spaced circumferential slots in axial alignment with said fingers, whereby rotational movement of the connector in one of said oscillatory directions is operable to cause driving contact of the fingers within a selected pair of slots to rotate said disk in one rotational direction, and rotational movement of the fingers in the opposite direction causes said fingers to rotate out of said slots into a pair of circumferentially adjacent slots without rotating said lost motion transmission disk and with renewed motion of said disk in said one rotational direction occurring upon a change in movement of said connector through said shaft in said one rotational direction;

wherein said gear train includes an input gear connected to the disk for rotary motion only in said one rotational direction.

21. The flossing device of claim 20, further including a ratchet tooth fixed to the housing, and wherein a series of projections are formed on a portion co-rotatable with the disk, said ratchet tooth including a first surface contactable with said projections to permit said projections to slide therepast in said one rotational direction, said tooth including a second surface lockable against one of the projections moving in the opposite rotational direction as a result of frictional contact between the fingers with the disk to thereby prevent reverse rotation of the input gear.

22. The flossing device of claim 21, wherein said input gear is a worm gear.

23. The flossing device of claim 22, wherein the worm gear has an axis of rotation in coaxial alignment with the output shaft rotational axis.

24. The flossing device of claim 22, wherein said gear train assembly further includes:

a speed reduction gear meshing with the worm gear;

a take-up spool drive gear meshing with the speed reduction gear, said drive gear being mounted on a support shaft projecting through the housing to the exterior thereof to support the floss take-up spool co-rotatably mounted thereon;

whereby said take-up spool is locked against rotation by the gear train assembly during non-rotation of said output shaft.

25. The flossing device of claim 24, wherein said take-up spool support shaft projects upward from the bottom wall of the housing substantially parallel to a second shaft supporting the speed reduction gear, said shafts defining axes of rotation for their respective gears which are perpendicular to and offset from the worm axis of rotation.

26. The flossing device of claim 19, wherein said output shaft rotates in one direction only, said gear train including:

a worm having an axis of rotation in coaxial alignment with said output shaft which is received directly in a rear portion of the worm, the rear portion being said connecting means;

a speed reduction gear meshing with said worm, said speed reduction gear being mounted within the housing for co-rotation on a shaft projecting upwardly through the housing top wall to directly support the take-up spool to rotate the same.

27. The flossing device of claim 26, wherein said ratchet mechanism is connected to the supply spool and comprises:

a first set of upward facing fixed teeth formed on one of the housing walls;

a second set of downward facing teeth contacting the first set, a hub projecting upward from said second set for co-rotation therewith;

a compression spring mounted to said hub for urging said second set against the first set;

said floss supply spool being mounted to the hub for co-rotation therewith;

whereby rotation of the supply spool in the unwinding direction occurs against the resistance of the spring biased first and second tooth sets, said resistance being yieldable against rotation of the take-up spool during actuation of the device but cooperating with the locked take-up spool during periods of deactivation to thereby tension the floss circuit to a predetermined extent.

28. The flossing device of claim 27, wherein said take-up spool is formed with a smaller diameter portion projecting downwardly towards the housing from a larger diameter cylindrical portion, said larger diameter portion being formed with an annular groove adapted to capture a free end of the floss to define one end of the flossing circuit.

29. The flossing device of claim 19, wherein said output shaft reciprocates within said housing in longitudinal strokes of predetermined length, said connecting means including:

a rack gear formed with rack teeth extending in coaxial alignment with said output shaft, and a plurality of flexible fingers projecting rearwardly from the rack gear and being operable to receive and wrap around the forward end of the output shaft, and slidable clip means longitudinally moveable to slide over the flexible fingers and press them against the output shaft forward end in clamping contact therewith.

30. The flossing device of claim 29, wherein said gear train assembly includes:

said rack gear;

a pinion mounted in said housing in meshing contact with the rack gear teeth for oscillatory rotation thereby;

a second gear mounted in said housing and having an axis of rotation parallel to the pinion gear in meshing contact therewith, said second gear thereby also oscillating in opposite rotational directions;

at least a pair of fingers projecting upwardly from said second gear;

a lost motion transmission disk coaxially mounted about the second gear and being formed with circumferentially spaced slots adapted to receive said fingers which engage end walls of associated of said slots to drive said lost motion transmission disk in one direction only corresponding to movement of the rack gear in one of its strokes, whereby movement of the rack gear in its opposite stroke causes the fingers to rotate relatively to said slots and out of said slots to engage circumferentially adjacent slots to thereby rotate said lost motion transmission disk upon renewed movement of said rack gear in said desired longitudinal stroke.

31. The flossing device of claim 30, further including a ratchet tooth fixed to the housing, and wherein a series of projections are formed on a portion co-rotatable with the disk, said ratchet tooth including a first surface contactable with said projections to permit said projections to slide therepast in said one rotational direction, said tooth including a second surface lockable against one of the projections moving in the opposite rotational direction as a result of frictional contact between the fingers with the disk to thereby prevent reverse rotation of the input gear.

32. The flossing device of claim 31, wherein said lost motion transmission disk includes a gear co-rotatable therewith thereby in one direction only which is in meshing contact with a take-up spool drive gear co-rotatable to rotate the take-up spool in the winding direction.

33. The flossing device of claim 32, wherein said lost motion transmission disk and said first and second gears are mounted on a common shaft extending vertically between top and bottom walls of the housing, opposite ends of said shaft being respectively received in said top and bottom walls.

34. The flossing device of claim 33, wherein said floss supply spool is driven in an unwinding rotational direction via rotation of the take-up spool only.

35. The flossing device of claim 34, wherein said ratchet mechanism is connected to the supply spool and comprises:

a first set of upward facing fixed teeth formed on one of the housing walls;

a second set of downward facing teeth contacting the first set, a hub projecting upward from said second set for co-rotation therewith;

a compression spring mounted to said hub for urging said second set against the first set;

said floss supply spool being mounted to the hub for co-rotation therewith;

whereby rotation of the supply spool in the unwinding direction occurs against the resistance of the spring biased first and second tooth sets, said resistance being yieldable against rotation of the take-up spool during actuation of the device but cooperating with the locked take-up spool during periods of deactivation to thereby tension the floss circuit to a predetermined extent.

36. The flossing device of claim 35, wherein the first tooth set is formed in a circular pattern about a post projecting upward from the housing wall at the center of the array, said post projecting upward through the hub through a bottom annular wall therein, a lower end of said spring being seated on said annular wall and extending upwardly around the post, and means engageable with the upper end of the post to define an upper spring seat for compressing the spring.

37. The flossing device of claim 36, wherein said second tooth set is arranged in a circular pattern in the lower surface of a disk from which the hub projects upwardly.

38. The flossing device of claim 37, further including key means between the hub and supply spool for detachably mounting the spool to the hub.

39. The flossing device of claim 17, wherein said floss supply spool is driven in an unwinding rotational direction via rotation of the take-up spool only.

40. The flossing device of claim 39, wherein said ratchet mechanism is connected to the supply spool and comprises:

a first set of upward facing fixed teeth formed on one of the housing walls;

a second set of downward facing teeth contacting the first set, a hub projecting upward from said second set for co-rotation therewith;

a compression spring mounted to said hub for urging said second set against the first set;

said floss supply spool being mounted to the hub for co-rotation therewith;

whereby rotation of the supply spool in the unwinding direction occurs against the resistance of the spring biased first and second tooth sets, said resistance being yieldable against rotation of the take-up spool during actuation of the device but cooperating with the locked take-up spool during periods of deactivation to thereby tension the floss circuit to a predetermined extent.

41. The flossing device of claim 40, wherein the first tooth set is formed in a circular pattern about a post projecting upward from the housing wall at the center of the array, said post projecting upward through the hub through a bottom annular wall therein, a lower end of said spring being seated on said annular wall and extending upwardly around the post, and means engageable with the upper end of the post to define an upper spring seat for compressing the spring.

42. The flossing device of claim 41, wherein said second tooth set is arranged in a circular pattern in the lower surface of a disk from which the hub projects upwardly.

43. The flossing device of claim 42, further including key means between the hub and supply spool for detachably mounting the spool to the hub.

44. The flossing device of claim 17, wherein said take-up spool is formed with a smaller diameter portion projecting downwardly towards the housing from a larger diameter cylindrical portion, said larger diameter portion being formed with an annular groove adapted to capture a free end of the floss to define one end of the flossing circuit.

45. The flossing device of claim 17, wherein said actuating mechanism includes a manually depressible trigger, said gear train assembly including:

an input gear rotated by said trigger;

a take-up spool drive gear mounted for co-rotation with said take-up spool;

a transfer gear meshing with said input gear and being operable to rotate said drive gear during depressing of said trigger; and a supply spool drive gear driven by said input gear and mounted for co-rotation with said supply spool to thereby rotate said supply spool in an unwinding direction during trigger actuation.

46. The flossing device of claim 45, wherein said supply gear is permanently meshed with the input gear and is thereby locked against rotational movement by the input gear when the trigger is not being depressed, said ratchet mechanism being connected to the take-up spool.

47. The flossing device of claim 46, wherein, during release of the depressed trigger, said input gear is operable to reversely rotate the supply gear through a predetermined arcuate interval, to remove slack from the floss circuit in cooperation with the take-up spool which is locked against reverse rotation by the ratchet mechanism.

48. The flossing device of claim 47, wherein said transfer gear is mounted on a tiltable shaft moveable between first and second positions as a result of meshing contact with the input gear, whereby when the trigger is in its deactivated position, said transfer gear is out of meshing contact with said take-up supply spool gear, depressing of said trigger causing the rotating input gear meshing with said transfer gear to rotate said transfer gear and index same into meshing contact with said take-up spool drive gear as said transfer gear support shaft is moved from its first position into a second tilted position, and wherein return movement of said trigger during release thereof is operable to reversely rotate said input gear which releases the transfer gear from the take-up spool drive gear and causes said transfer gear support shaft to tilt back into its first position.

49. The flossing device of claim 47, wherein said trigger is spring biased with a spring to project outwardly from the housing, whereby depressing of said trigger occurs against spring bias.

50. The flossing device of claim 49, wherein said trigger mechanism is in the form of a substantially flat plate extending generally parallel to the bottom wall of the housing, said trigger plate including a center or pivot portion through which a trigger pin extends in a substantially vertical direction.

51. The flossing device of claim 50, wherein the depressible portion of the trigger plate is a distal portion adapted to protrude through a slot in a housing side wall, said spring contacting another distal portion of the plate which projects rearwardly from the trigger pin so as to urge the depressible trigger portion outwardly through the slotted wall.

52. The flossing device of claim 50, wherein a slot is formed in the trigger plate between said first and second distal portions to receive the supply spool support shaft and thereby provide clearance between said trigger plate with said shaft as the trigger is manually depressed.

53. The flossing device of claim 50, wherein said trigger plate includes a third distal portion located forwardly of the trigger pin which has a profiled cam surface adapted to engage a cam follower mounted on the transfer gear support shaft to spring bias the transfer gear and its shaft into the first position during periods of deactivation of the trigger.

54. The flossing device of claim 47, wherein said ratchet mechanism includes a first ratchet member mounted on the take up spool supply shaft for co-rotation therewith in the winding direction, and a second ratchet member provided with a set of annular inwardly extending teeth fixedly mounted to the housing about the take-up spool shaft, said first ratchet member extending within the second member and being operable to lockingly engage the annular teeth during reverse rotation of the take-up spool to prevent the occurrence of said reverse rotation.

55. The flossing device of claim 45, wherein all of the gears in said gear train assembly are mounted on vertical axes of rotation.

56. A flossing device, comprising:

a floss circuit including a take-up spool and a supply spool between which floss extends;

an actuating mechanism for rotating the take-up spool to wind used floss thereon and simultaneously advance fresh floss into a flossing location of the circuit;

means for locking the take-up and supply spools during periods of deactivation of the actuating mechanism;

wherein, prior to deactuating movement of said actuating mechanism, said actuating mechanism is operable to reversely rotate the supply spool when the take up spool is already locked to thereby remove slack from the floss circuit and provide tension therein.

57. The flossing device of claim 56, further comprising a housing to which the take-up spool and supply spool are mounted, said take-up spool being located outside of the housing.

58. A method of flossing with a flossing device which is attachable to a hand-held motorized toothbrush handle equipped with a motor from which projects an output shaft, said flossing device comprising a housing provided with a take-up spool and a supply spool between which floss extends in a floss circuit, comprising the steps of attaching the housing to the toothbrush handle so that the output shaft thereof extends into the housing in driving contact with an actuating mechanism which rotates the take-up spool during periods of actuation; flossing between a pair of teeth by inserting a flossing location of the flossing circuit into the mouth without operating the motor so that the floss in the flossing mechanism is stationary relative thereto; removing the flossing location from between said pair of teeth; activating the motor to actuate the actuating mechanism to rotate the take-up spool and advance the spend floss from the flossing location which allows fresh floss to move into the flossing location; deactivating the motor and reinserting the flossing location to clean another pair of teeth; and repeating the above steps until flossing is complete.

* * * * *